United States Patent
Chan et al.

(10) Patent No.: US 12,275,995 B2
(45) Date of Patent: Apr. 15, 2025

(54) *LYSINIBACILLUS SPHAERICUS* AND ASPIRIN CHEMOPREVENTION OF COLORECTAL CANCER

(71) Applicant: The Chinese University of Hong Kong, Hong Kong (CN)

(72) Inventors: Francis Ka Leung Chan, Hong Kong SAR (CN); Jun Yu, Ma On Shan (CN)

(73) Assignee: The Chinese University of Hong Kong, Hong Kong SAR (CN)

( * ) Notice: Subject to any disclaimer, the term of this patent is extended or adjusted under 35 U.S.C. 154(b) by 481 days.

(21) Appl. No.: 17/078,036

(22) Filed: Oct. 22, 2020

(65) Prior Publication Data

US 2021/0123106 A1 Apr. 29, 2021

Related U.S. Application Data

(60) Provisional application No. 62/925,040, filed on Oct. 23, 2019.

(51) Int. Cl.
*C12Q 1/68* (2018.01)
*C12Q 1/6886* (2018.01)
*C12Q 1/689* (2018.01)

(52) U.S. Cl.
CPC ........... *C12Q 1/6886* (2013.01); *C12Q 1/689* (2013.01); *C12Q 2531/113* (2013.01)

(58) Field of Classification Search
None
See application file for complete search history.

(56) References Cited

PUBLICATIONS

Zoetendal et al., The ISME Journal (2012) 6, 1415-1426 (Year: 2012).*
Burke 1983. Current Microbiology, vol. 9, p. 62-79. (Year: 1983).*
Zhao. Gut microbiota modulates the chemopreventive efficacy of aspirin on colorectal cancer through impact on aspirin bioavailability (Order No. 27662587). Available from ProQuest Dissertations & Theses Global. (2308195090). 2019. (Year: 2019).*
Olina Biochemistry (Moscow), 2018, vol. 83, No. 5, pp. 483-497. (Year: 2018).*
Sully Current Opinion in Microbiology 2016, 33:47-55 (Year: 2016).*
Vogel Molecular Microbiology. 2020;113:550-559. (Year: 2020).*
Jani BiomedicinesBiomedicines 2021, 9, 416. https://doi.org/10.3390/biomedicines9040416 12 pages (Year: 2021).*
McDonald Jan. 1984; 130(1):203-208. Abstract Only (Year: 1984).*
Fu et al. BMC Microbiology (2017) 17:116; 8 pages (Year: 2017).*
Leon, D.C.; Dussan, J.Lysinibacillus sphaericus III(3)7 andPlasmid Vector pMK4: New Challenges in Cloning Platforms. Microbiol. Res. 2021, 12, 455-479. https://doi.org/10.3390/microbiolres/1202003125 pages. (Year: 2021).*
Frank et al. Current Opinion in Gastroenterology 2008, 24:4-10 (Year: 2008).*
Mandal et al. Genomics Proteomics Bioinformatics 13 (2015) 148-158 (Year: 2015).*
NIH, National Cancer Institute, Dictionary of cancer terms, definition of drug, obtained Feb. 22, 2024, from https://www.cancer.gov/publications/dictionaries/cancer-terms/def/drug. 1 page. (Year: 2024).*
NIH, National Cancer Institute, Dictionary of cancer terms, definition of antibiotic, obtained Feb. 22, 2024, from https://www.cancer.gov/ publications/dictionaries/cancer-terms/def/antibiotic. 1 page. (Year: 2024).*
Arnold, et al., "Global patterns and trends in colorectal cancer incidence and mortality," Gut, vol. 66(4), pp. 683-691 (2017).
Thun, et al., "The role of aspirin in cancer prevention," Nat Rev Clin Oncol., vol. 9(5), pp. 259-267 (2012).
Drew, et al., "Aspirin and colorectal cancer: the promise of precision chemoprevention," Nat Rev Cancer., vol. 16(3), pp. 173-186 (2016).
Baron, et al., "A Randomized Trial of Aspirin to Prevent Colorectal Adenomas," N Engl J Med, vol. 348, pp. 891-899 (2003).
Burn, et al., "Long-term effect of aspirin on cancer risk in carriers of hereditary colorectal cancer: an analysis from the CAPP2 randomised controlled trial," Lancet, vol. 378, pp. 2081-2087 (2011).
Hull, et al., "Eicosapentaenoic acid and aspirin, alone and in combination, for the prevention of colorectal adenomas (seAFOod Polyp Prevention trial): a multicentre, randomised, double-blind, placebo-controlled, 2×2 factorial trial," Lancet; vol. 392: pp. 2583-2594 (2018).
Chubak, et al., "Aspirin Use for the Prevention of Colorectal Cancer: An Updated Systematic Evidence Review for the U.S. Preventive Services Task Force," Evidence Syntheses, No. 133, Rockville (MD): Agency for Healthcare Research and Quality (US), 127 pages (2015).
Rothwell, et al., "Effects of aspirin on risks of vascular events and cancer according to bodyweight and dose: analysis of individual patient data from randomised trials," Lancet; vol. 392, pp. 387-399 (2018).
Chan, et al., "Aspirin Dose and Duration of Use and Risk of Colorectal Cancer in Men," Gastroenterology, vol. 134, pp. 21-28 (2008).
Yu, et al., "Metagenomic analysis of faecal microbiome as a tool towards targeted non-invasive biomarkers for colorectal cancer," Gut, vol. 66, pp. 70-78 (2017).
Nakatsu, et al., "Gut mucosal microbiome across stages of colorectal carcinogenesis," Nat Commun., vol. 6(8727), 9 pages (2015).
Tsoi, et al., "*Peptostreptococcus anaerobius* Induces Intracellular Cholesterol Biosynthesis in Colon Cells to Induce Proliferation and Causes Dysplasia in Mice," Gastroenterology, vol. 152, pp. 1419-1433 (2017).

(Continued)

*Primary Examiner* — Juliet C Switzer
(74) *Attorney, Agent, or Firm* — Kilpatrick Townsend & Stockton LLP

(57) ABSTRACT

The present invention provides methods for assessing the likelihood of effectiveness of aspirin-based chemoprotection against colorectal cancer among individuals as well as methods for improving aspirin-based chemoprotection against colorectal cancer. Kits useful for such methods are also provided.

15 Claims, 25 Drawing Sheets

(56) References Cited

PUBLICATIONS

Figure 1A:
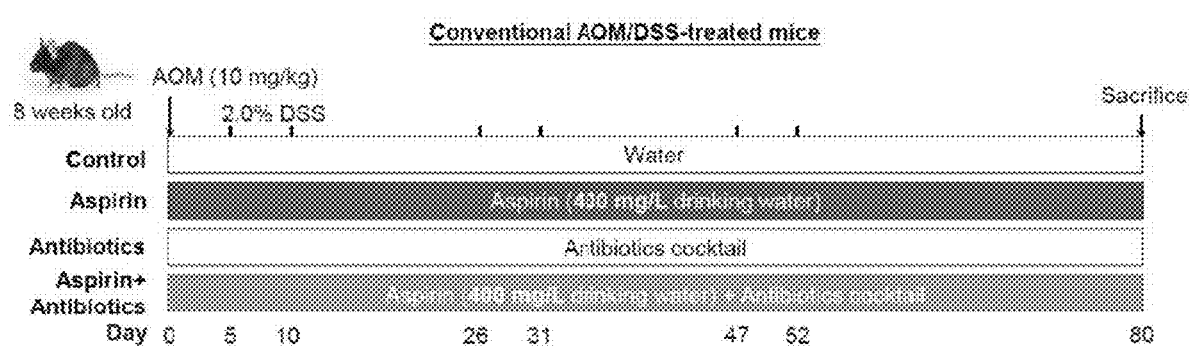

Wong, et al., "Gavage of Fecal Samples From Patients With Colorectal Cancer Promotes Intestinal Carcinogenesis in Germ-Free and Conventional Mice," Gastroenterology, vol. 153, pp. 1621-1633 (2017).

Long, et al., "*Peptostreptococcus anaerobius* promotes colorectal carcinogenesis and modulates tumour immunity," Nature Microbiology, vol. 4, pp. 2319-2330 (2019).

Wong, et al., "Gut microbiota in colorectal cancer: mechanisms of action and clinical applications," Nature Reviews Gastroenterology & Hepatology, vol. 16, pp. 690-704 (2019).

David, et al., "Diet rapidly and reproducibly alters the human gut microbiome," Nature, vol. 505(7484), pp. 559-563 (2014).

Thaiss, et al., "Microbiota Diurnal Rhythmicity Programs Host Transcriptome Oscillations," Cell, vol. 167, Issue 6, pp. 1495-1510 (2016).

Wang, et al., "The intestinal microbiota regulates body composition through NFIL3 and the circadian clock," Science, vol. 357, pp. 912-916 (2017).

Maier, et al., "Extensive impact of non-antibiotic drugs on human gut bacteria," Nature, vol. 555(7698), pp. 623-628 (2018).

Wu, et al., "Metformin alters the gut microbiome of individuals with treatment-naive type 2 diabetes, contributing to the therapeutic effects of the drug," Nature Medicine, vol. 23(7), pp. 850-858 (2017).

Cheng, et al., "Effects of none-steroidal anti-inflammatory and antibiotic drugs on the oral immune system and oral microbial composition in rats," Biochem Biophys Res Commun., vol. 507(1-4), pp. 420-425 (2018).

Rogers, et al., "The influence of non-steroidal anti-inflammatory drugs on the gut Microbiome," Clin Microbiol Infect., vol. 22, pp. 178.e1-178.e9.(2016).

Koppel, et al., "Chemical transformation of xenobiotics by the human gut microbiota," Science, vol. 356, Issue 6344, 11 pages (2017).

Sousa, et al., "On the Colonic Bacterial Metabolism of Azo-Bonded Prodrugs of 5-Aminosalicylic Acid," J Pharm Sci., vol. 103(10), pp. 3171-3175. (2014).

Haiser, et al., "Predicting and Manipulating Cardiac Drug Inactivation by the Human Gut Bacterium *Eggerthella lenta*," Science, vol. 341(6143), pp. 295-298 (2013).

Kim, et al., "Reduced metabolic activity of gut microbiota by antibiotics can potentiate the antithrombotic effect of aspirin," Biochemical Pharmacology, vol. 122, pp. 72-79 (2016).

Reddy, et al., "Inhibitory effect of aspirin on azoxymethane-induced colon carcinogenesis in F344 rats," Carcinogenesis, vol. 14, No. 8, pp. 1493-1497 (1993).

Trinder, "Rapid Determination of Salicylate in Biological Fluids," Biochem J., vol. 57(2), pp. 301-303 (1954).

Nakatsu, et al., "Alterations in Enteric Virome Are Associated With Colorectal Cancer and Survival Outcomes," Gastroenterology, vol. 155, pp. 529-541 (2018).

Edalatian, et al., "Microbial diversity of the traditional Iranian cheeses Lighvan and Koozeh, as revealed by polyphasic culturing and culture-independent approaches," Dairy Sci & Technol., vol. 92, pp. 75-90 (2012).

Zarrinpar, et al., "Antibiotic-induced microbiome depletion alters metabolic homeostasis by affecting gut signaling and colonic metabolism," Nature Communications, vol. 9, Article No. 2872, pp. 1-13 (2018).

Xu, et al., "Suppression of inducible cyclooxygenase 2 gene transcription by aspirin and sodium salicylate," Proc. Natl. Acad. Sci. USA, vol. 96, pp. 5292-5297 (1999).

Fiebich, et al., "Effects of caffeine and paracetamol alone or in combination with acetylsalicylic acid on prostaglandin E2 synthesis in rat microglial cells," Neuropharmacology, vol. 39, pp. 2205-2213 (2000).

Hollander, et al., "Intestinal absorption of aspirin Influence of pH, taurocholate, ascorbate, and ethanol," The Journal of Laboratory and Clinical Medicine, vol. 98(4), abstract (1981).

Rodriguez, et al., "Reduced Risk of Colorectal Cancer among Long-Term Users of Aspirin and Nonaspirin Nonsteroidal Antiinflammatory Drugs," Epidemiology, vol. 12, No. 1, pp. 88-93 (2001).

Shi, et al., "Polyphosphate kinase of *Lysinibacillus sphaericus* and its effects onaccumulation of polyphosphate and bacterial growth," Microbiological Research, vol. 172, pp. 41-47 (2015).

Ahmed, et al., "Proposal of *Lysinibacillus boronitolerans* gen. nov. sp. nov., and transfer of *Bacillus fusiformis* to *Lysinibacillus fusiformis* comb. nov. and *Bacillus sphaericus* to *Lysinibacillus sphaericus* comb. nov.," International Journal of Systematic and Evolutionary Microbiology, vol. 57, pp. 1117-1125 (2007).

Li, et al., "*Streptococcus thermophilus* inhibits colorectal tumorigenesis through secreting ß- Galactosidase," Gastroenterology., S0016-5085(20)35129-5., 50 pages (2020).

Konishi, et al., "Probiotic-derived ferrichrome inhibits colon cancer progression via JNK-mediated apoptosis," Nature Communications, vol. 7, Article No. 12365, pp. 1-12 (2016).

Dai, et al., "Multi-cohort analysis of colorectal cancer metagenome identified altered bacteria across populations and universal bacterial markers," Microbiome, vol. 6:70, 12 pages (2018).

Ishikawa, et al., "Randomized trial of dietary fiber and *Lactobacillus casei* administration for prevention of colorectal tumors," Int. J. Cancer, vol. 116, pp. 762-767 (2005).

Rafter , et al., "Dietary synbiotics reduce cancer risk factors in polypectomized and colon cancer patients," Am J Clin Nutr, vol. 85, pp. 488-496 (2007).

\* cited by examiner

LYSINIBACILLUS SPHAERICUS AND ASPIRIN CHEMOPREVENTION OF COLORECTAL CANCER

RELATED APPLICATIONS

This application claims priority to U.S. Provisional Patent Application No. 62/925,040, filed Oct. 23, 2019, the contents of which are hereby incorporated by reference in the entirety for all purposes.

BACKGROUND OF THE INVENTION

Colorectal cancer (CRC) is the third most common cancer and the third leading cause of cancer mortality worldwide. Both the incidence and death rate of CRC are increasing rapidly and maintaining an upward trend in Asian countries, despite ongoing efforts devoted towards the control of new CRC incidence. The global persistence of CRC necessitates a paradigm shift in its management strategy, from clinical treatment to preclinical prevention. Aspirin has emerged as a promising agent for chemoprevention of colorectal adenoma and cancer. For largely unknown reasons, however, the chemopreventive efficacy of aspirin varies significantly among individuals. Thus, there exists an urgent need for new and reliable methods to assess among patients the likelihood of effective chemopreventive measures by aspirin administration against CRC risk.

The invention describes a bacterial marker for the prediction of the chemopreventive efficacy of aspirin against CRC. *Lysinibacillus sphaericus*, an aspirin-degrading microbe, is found to be useful in the prediction of personalized CRC chemoprevention by aspirin. More specifically, the present disclosure relates to: (1) the effectiveness of CRC chemoprevention by aspirin was demonstrated in CRC mouse models with gut microbiota depletion, but not in mice with intact gut microbiota. Consistently, aspirin significantly inhibited intestinal tumorigenesis in germ-free mice. The inhibitory effect was, however, abolished by conventionalization of the germ-free mice. (2) Plasma level of aspirin was higher in microbiota-depleted mice. Fecal bacteria possessed the degrading ability on aspirin and identified *Lysinibacillus sphaericus* as a microbe that degrades aspirin. (3) Germ-free mice monocolonized with *Lysinibacillus sphaericus* showed decreased plasma aspirin levels relative to germ-free control mice. (4) The efficacy of aspirin-mediated CRC chemoprevention was demonstrated with increased aspirin dosage in conventional microbiota-intact mice. The efficacy was dampened with increased abundance of *Lysinibacillus sphaericus*.

As such, this discovery provides important and improved means for the prevention of CRC. It provides useful insight for the varied clinical effectiveness of aspirin on human CRC chemoprevention. It allows for the prediction of efficacy in personalized CRC chemoprevention by aspirin, based on gut microbiota composition, as well as for improvement of efficacy of CRC chemoprevention by aspirin via suppression or elimination of *Lysinibacillus sphaericus* in a recipient's digestive tract.

BRIEF SUMMARY OF THE INVENTION

The present inventors have discovered the previously unknown but very important correlation between the presence and abundance of the bacterial species *Lysinibacillus sphaericus* in a person's digestive tract and the effectiveness of aspirin-mediated chemoprotection against colorectal cancer (CRC) risk. Thus, the first aspect of the present invention provides a method for determining protective measure against colorectal cancer (CRC) risk in an individual. The method includes these steps: (a) detecting the presence or absence of *Lysinibacillus sphaericus* in a stool sample taken from the individual; (b) determining aspirin administration as likely effective in the individual as a protective measure against CRC when *Lysinibacillus sphaericus* is not detected in the stool sample, and administering to the individual an effective amount of aspirin; and (c) determining aspirin administration as unlikely effective in the individual as a protective measure against CRC when *Lysinibacillus sphaericus* is detected in the stool sample, and providing to the individual an alternative protective measure against CRC different from aspirin administration or administering to the individual an effective amount of aspirin just after or at the same time of providing a treatment that suppresses or eliminates *Lysinibacillus sphaericus* in the individual. Depending on the circumstances, such treatment may include the administration of an antibacterial agent that is specific for suppressing or eliminating *Lysinibacillus sphaericus* (such as those described herein) or a broad spectrum antibiotic.

In some embodiments, the individual has a family history of CRC or has been diagnosed with colon polyps or cysts. In some embodiments, step (a) of the method comprises a polymerase chain reaction (PCR) for measuring the level of a polynucleotide sequence of *Lysinibacillus sphaericus*, for example, the PCR is a reverse transcription polymerase chain reaction (RT-PCR). In some embodiments, the level of *Lysinibacillus sphaericus* 16S rRNA is measured in the RT-PCR. In some embodiments, the method further comprises a step of determine the level of one or more of *Bifidobacterium pseudolongum, B. breve, B. animalis, Lactobacillus reuteri, L. gasseri,* and *L. johnsonii* in the stool sample. In some embodiments, the method may further comprise, after the individual has been provided a treatment that suppresses or eliminates *Lysinibacillus sphaericus* in the individual, a step of detecting *Lysinibacillus sphaericus* in a second stool sample taken from the individual. In some embodiments, the inhibitor is a small inhibitory RNA or antisense oligonucleotide specifically targeting at least one gene of *Lysinibacillus sphaericus*, or an expression cassette directing expression of the inhibitory RNA, or a viral vector comprising the expression cassette. In some embodiments, the expression cassette is comprised within a viral particle.

In a second aspect, the present invention provides a method for assessing likelihood of effective reduction of CRC risk by aspirin administration among individuals. The method includes the steps of: (a) measuring *Lysinibacillus sphaericus* level in a first stool sample taken from a first individual and in a second stool sample taken from a second individual; (b) detecting the *Lysinibacillus sphaericus* level in the first sample as being higher than the *Lysinibacillus sphaericus* level in the second sample; and (c) determining the second individual as having a higher likelihood of effective reduction of CRC risk by aspirin administration than the first individual.

In some embodiments, the method further comprises, subsequent to step (c), administering to the second individual an effective amount of aspirin. In some embodiments, herein step (a) comprises a polymerase chain reaction (PCR), e.g., a reverse transcription polymerase chain reaction (RT-PCR). In some embodiments, the individuals have a family history of CRC or have been diagnosed with colon polyps or cysts. In some embodiments, the method further comprises, subsequent to step (c), administering to the first individual an inhibitor of *Lysinibacillus sphaericus* just prior to or at same time of administering to the first individual an effective amount of aspirin. In some embodiments, the method further comprises a step of determine the level of one or more of *Bifidobacterium pseudolongum, B. breve, B. animalis, Lactobacillus reuteri, L. gasseri*, and *L. johnsonii* in the stool samples.

In a third aspect, the present invention provides a method for enhancing efficacy of reduction of CRC risk by aspirin administration in an individual, comprising administering to the individual an effective amount of an inhibitor of *Lysinibacillus sphaericus* just prior to or at the same time of administering to the individual an effective amount of aspirin. In some embodiments, the method further comprises determining *Lysinibacillus sphaericus* level in a stool sample taken from the individual before and after administering the inhibitor. In some embodiments, the inhibitor is a small inhibitory RNA or antisense oligonucleotide specifically targeting at least one gene of *Lysinibacillus sphaericus*, or an expression cassette directing expression of the inhibitory RNA, or a viral vector comprising the expression cassette.

In a fourth aspect, the present invention provides a kit for assessing likelihood of effective reduction of CRC risk by aspirin administration. The kit includes (1) a first container containing one or more reagents for measuring *Lysinibacillus sphaericus* level in a stool sample taken from an individual being assessed; and (2) a second container containing a composition comprising an amount of *Lysinibacillus sphaericus* corresponding to a cut-off value. In some embodiments, the first container comprises PCR reagents for measuring the level of one or more genes of *Lysinibacillus sphaericus*. In some embodiments, the kit may further comprise a third container comprising an inhibitor of *Lysinibacillus sphaericus*. For example, the inhibitor may be an antibacterial agent that is specific for suppressing or eliminating *Lysinibacillus sphaericus* (such as those described herein) or a broad spectrum antibiotic. In some embodiments, the kit further comprises an instruction manual providing information for a user to use the kit for its intended purposes.

BRIEF DESCRIPTION OF THE DRAWINGS

FIG. 1A-FIG. 1F. Depletion of gut microbiota enhances the effect of aspirin on the prevention of CRC. (FIG. 1A) Schematic overview of treatments in AOM/DSS-induced cancer model. After initial AOM injection (10 mg/kg), three cycles of 2.0% DSS was given in drinking water before sacrifice at day 80. n=25 for each group. (FIG. 1B) Representative images of large intestines (left panels) and hematoxylin-eosin staining of adenomas (right panels) in AOM/DSS-treated mice. Each red arrow points at one tumor location. (FIG. 1C) Tumor number and tumor load in AOM/DSS-treated mice, Unpaired Student's t test. (FIG. 1D) Schematic overview of treatments in APC$^{min/+}$ cancer model. n=16 for control group, n=14 each for Aspirin, Antibiotics and Aspirin+Antibiotics groups. (FIG. 1E) Representative images of large intestines (left panels) and hematoxylin-eosin staining of adenomas (right panels) in APC$^{min/+}$ mice. Each red arrow points at one tumor location. (FIG. 1F) Tumor number (left panel) and tumor load (right panel) in APC$^{min/+}$ mice, Mann-Whitney U test. AOM, azoxymethane; DSS, dextran sulfate sodium.

FIG. 2A-FIG. 2E. Conventionalization of germ-free mice impairs the chemopreventive efficacy of aspirin in germ-free mice. (FIG. 2A) Schematic overview of treatments in AOM/DSS-treated germ-free mice. After initial AOM injection (10 mg/kg), three cycles of 2.0% DSS was administered to mice in drinking water before sacrifice at day 80. Half of germ-free mice were conventionalized by placing their cages out of germ-free environment before AOM injection. n=14 for GF-Control group, n=16 for GF-Aspirin group, n=21 for cGF-Control group and n=29 for cGF-Aspirin group. (FIG. 2B) Representative images of large intestines (left panels) and hematoxylin-eosin staining of adenomas (right panels) in AOM/DSS-treated germ-free mice. Each red arrow points at one tumor location. (FIG. 2C) Tumor number (left panel) and tumor load (right panel) in AOM/DSS-treated germ-free mice. (FIG. 2D) Representative images of large intestines (left panels) and hematoxylin-eosin staining of adenomas (right panels) in AOM/DSS-treated conventionalized mice. Each red arrow points at one tumor location. (FIG. 2E) Tumor number (left panel) and tumor load (right panel) in AOM/DSS-treated conventionalized mice, Unpaired Student's t test. AOM, azoxymethane; DSS, dextran sulfate sodium; GF, germ-free; cGF, conventionalization of germ-free.

FIG. 3A-FIG. 3C. The suppressive effects of aspirin on COX-2 and PGE2 are enhanced in gut microbiota-depleted mice and germ-free mice. (FIG. 3A) Relative COX-2 mRNA level in distal colonic tissues (left panel) and plasma PGE2 (right panel) level in in AOM/DSS-treated mice. n=10 for each group. (FIG. 3B) Relative COX-2 mRNA level in distal colonic tissues (left panel) (n=16 for Control group, n=14 each for Aspirin, Antibiotics and Aspirin+Antibiotics groups), and plasma PGE2 level (right panel) (n=10 each for Control and Aspirin+Antibiotics groups, n=9 for Aspirin group, n=11 for Antibiotics group) in APC$^{min/+}$ mice, unpaired Student's t test. (FIG. 3C) Relative COX-2 mRNA level in distal colonic tissues (left panel) and PGE2 (right panel) level in plasma in germ-free mice. n=10 for each group, unpaired Student's t test. COX-2, cyclooxygenase-2; PGE2, prostaglandin E2; AOM, azoxymethane; DSS, dextran sulfate sodium; GF, germ-free; cGF, conventionalization of germ-free.

FIG. 4A-FIG. 4F. Depletion of microbiota is associated with an elevation of aspirin bioavailability. (FIG. 4A) Schematic overview of experimental design for studying the impact of microbiota on aspirin bioavailability. APC$^{min/+}$ mice with or without pre-antibiotic treatment for five days were given aspirin (10 mg/kg) by gavage (n=10 for each group). Blood samples were collected at 0.5 h and 1 h post administration. (FIG. 4B) Product ion spectra of aspirin in UHPLC-Q-TOF/MS analysis. (FIG. 4C) Counts of aspirin in plasma samples at 0.5 h (left panel) and 1 h (right panel). (FIG. 4D) Quantitative analysis of aspirin level in plasma samples. (FIG. 4E) Schematic overview of experimental design for studying the effect of increased bioavailability on chemoprevention. AOM/DSS-treated mice were given a higher dose of aspirin (1200 mg/L in drinking water) than used in FIG. 1A. (FIG. 4F) Tumor number (left panel) and tumor load (right panel) in mice, unpaired Student's t test. UHPLC-Q-TOF/MS, ultra-high-performance liquid chromatography-quadrupole time-of-flight mass spectrometry; AOM, azoxymethane; DSS, dextran sulfate sodium.

FIG. 5A-FIG. 5D. Gut aerotolerant microbes are associated with aspirin degradation. (FIG. 5A) Schematic overview of experimental design for studying the impact of microbiota on aspirin in vitro (n=5 for each group). (FIG. 5B) Arylesterase activity in the medium exposed to fecal samples under aerobic (left panel) and anaerobic (right panel) condition, two-way ANOVA test. (FIG. 5C) Relative level of salicylic acid in aspirin-containing culture medium post aerobic incubation (upper panel) and anaerobic incubation (lower panel) with fecal samples, two-way ANOVA test. (FIG. 5D) Relative level of aspirin in aspirin-containing culture medium post aerobic (right panel) and anaerobic incubation (left panel) with fecal samples, Mann-Whitney U test. OD, optical density.

FIG. 6A-FIG. 6H. *Lysinibacillus sphaericus* degrades aspirin and impairs its chemopreventive efficacy. (FIG. 6A) Schematic overview of procedures used in screening microbes with degradation effect on aspirin in vitro. (FIG. 6B) Relative level of aspirin in aspirin-containing culture medium post aerobic incubation with *L. sphaericus* and *Staphylococcus xylosus*, two-way ANOVA test. (FIG. 6C) Schematic overview of experimental design for studying the effect of *L. sphaericus* on aspirin bioavailability in germ-free mice. (FIG. 6D) Plasma aspirin level at 0.5 h (left panel) and 1 h (right panel). (FIG. 6E) Quantitative analysis of plasma aspirin level, unpaired Student's t test. (FIG. 6F) Schematic overview of experimental design for studying the impact of *L. sphaericus* on CRC chemoprevention. AOM/DSS-treated mice were gavaged with *L. sphaericus*. Aspirin dosage (1200 mg/L in drinking water) proved to be effective on chemoprevention in FIG. 4E was used. (FIG. 6G) Tumor number (left panel) and tumor load (right panel) in mice, unpaired Student's t test. (FIG. 6H) Metagenomic analysis of the presence of *L. sphaericus* in healthy subjects and adenoma patients. CM, cooked-meat; BHI, brain heart infusion; MALDI-TOF/MS, matrix-assisted laser desorption/ionization time of flight mass spectrometry; *L. shaericus, Lysinibacillus sphaericus; S. xylosus, Staphylococcus xylosus*.

Figure 7A:
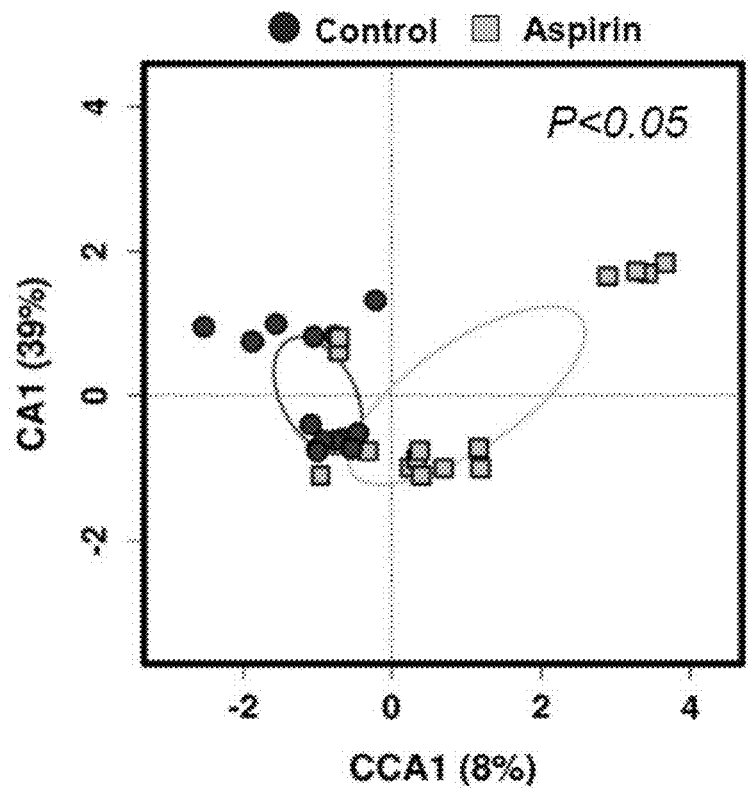
Figure 7B:
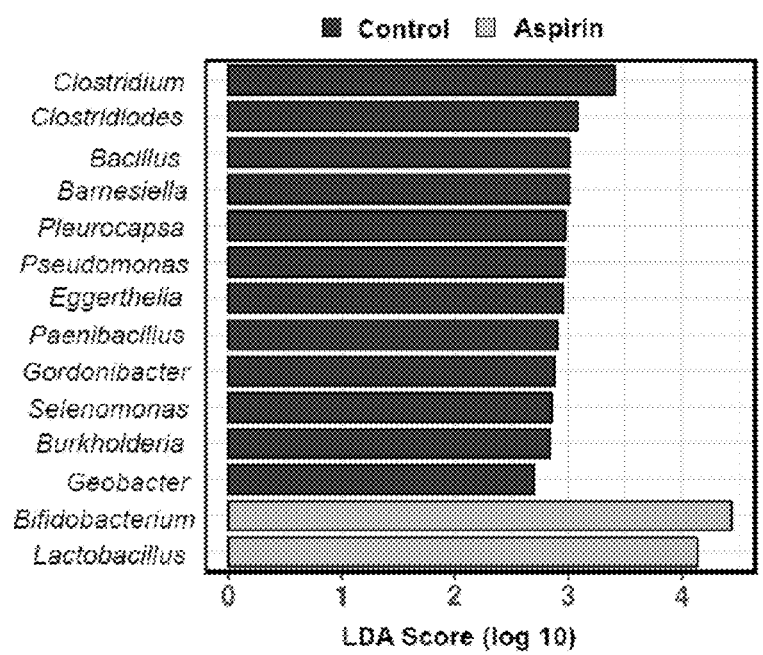
Figure 7C:
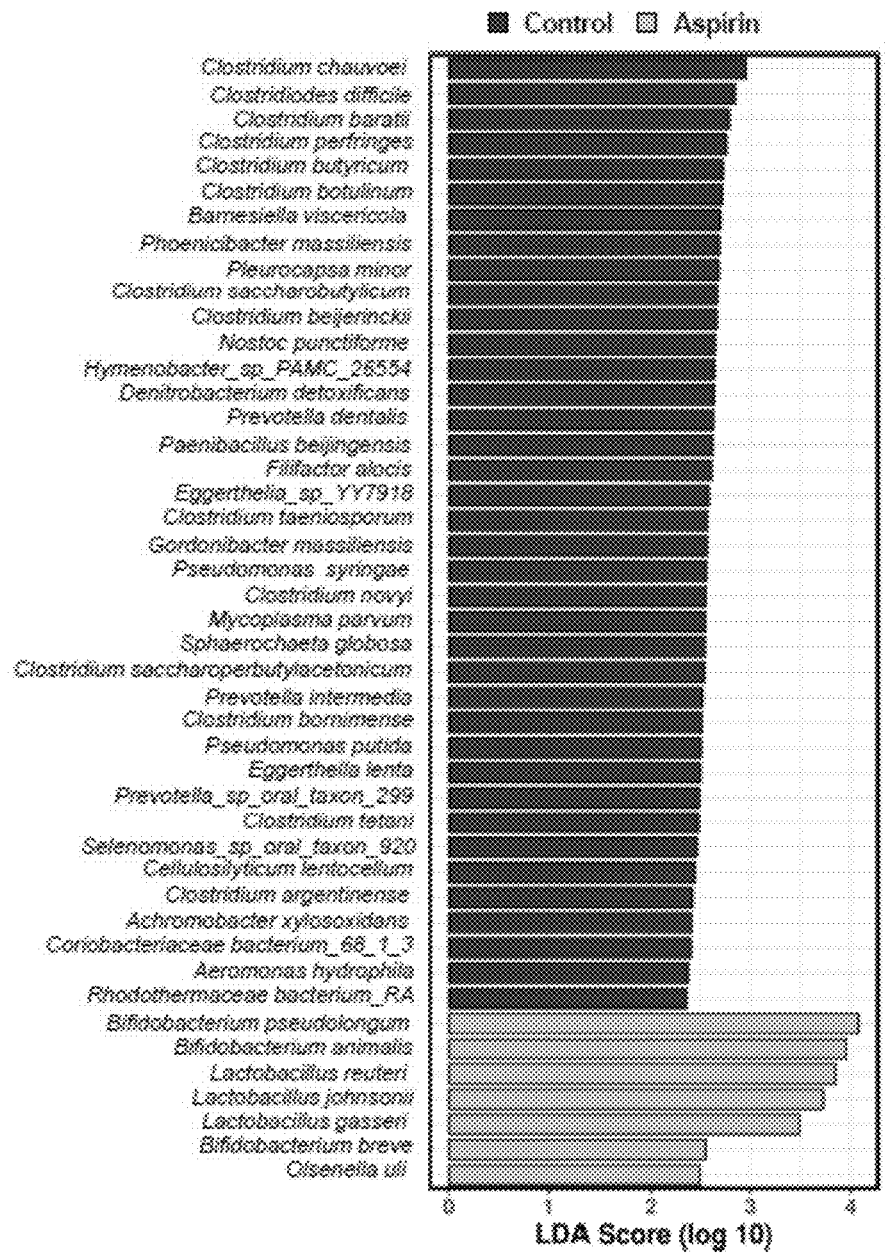

FIG. 7A-FIG. 7C. Aspirin treatment enriches protective bacteria in the gut. (FIG. 7A) Multivariate component analysis of aspirin-mediated impact on bacterial composition. (FIG. 7B) Linear discriminant analysis of aspirin-induced enrichment of bacteria at genus level. (FIG. 7C) Linear discriminant analysis of aspirin-induced enrichment of bacteria at species level.

Figure 8:
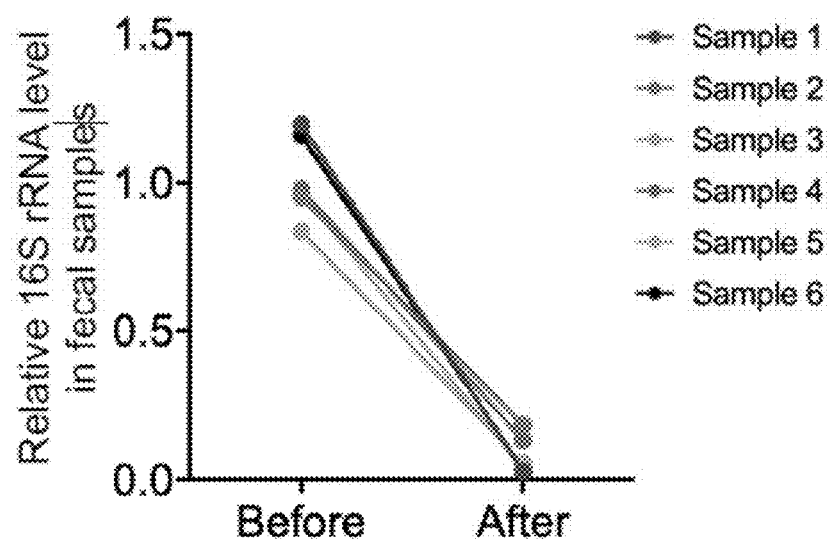

FIG. 8. Antibiotics cocktail was effective in depleting the gut microbiota. Each color represents fecal samples from antibiotics-treated mice before and after antibiotic treatment.

Figure 9A:
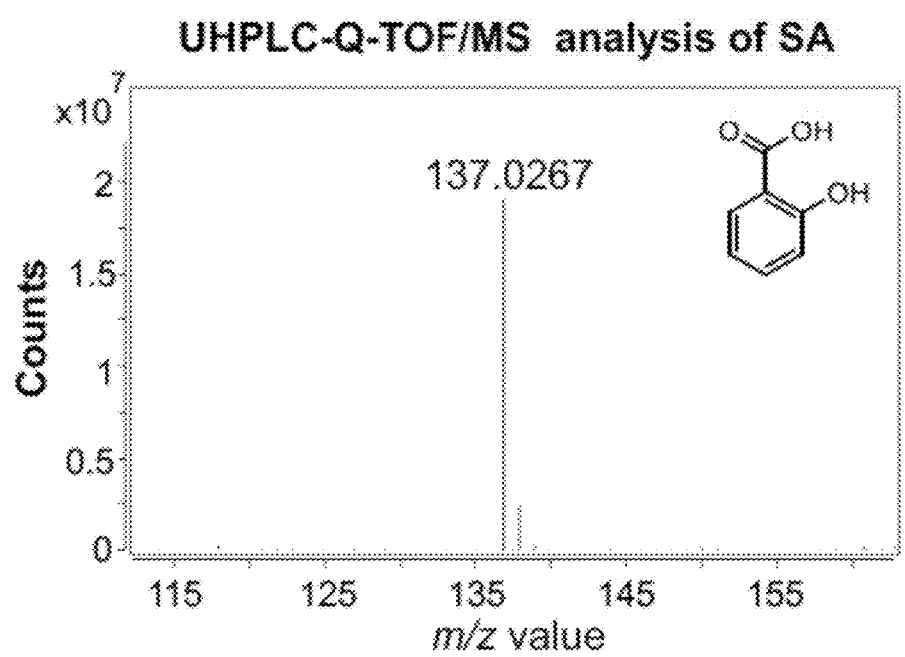
Figure 9B:
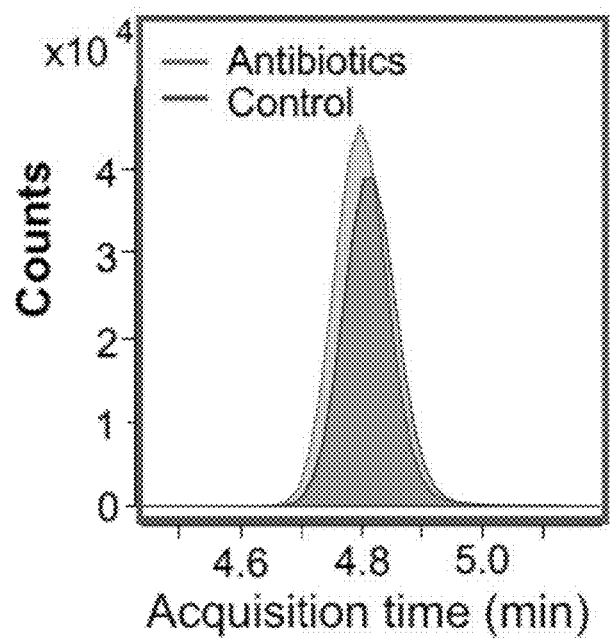
Figure 9C:
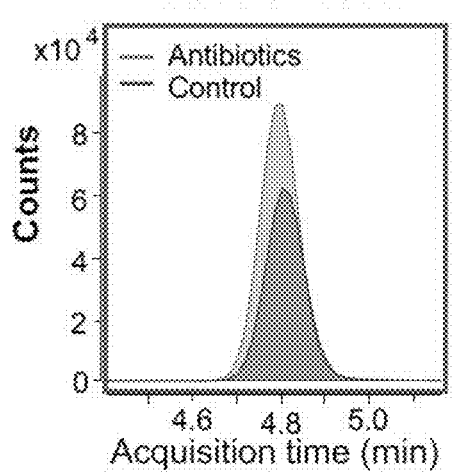
Figure 9C:
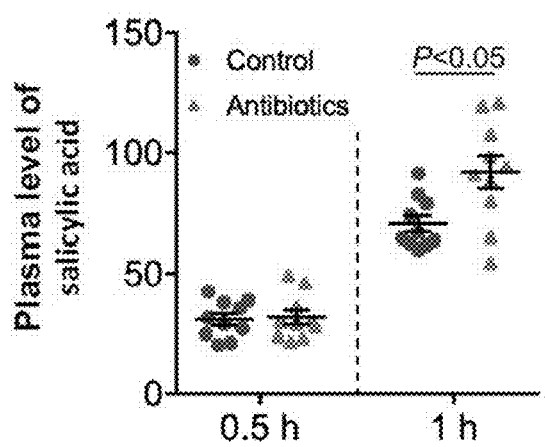

FIG. 9A-FIG. 9C. Plasma level of salicylic acid in mice with and without antibiotic treatment. (FIG. 9A) Product ion spectra of salicylic acid in UHPLC-Q-TOF/MS analysis. (FIG. 9B) Counts of salicylic acid in plasma samples at 0.5 h (left panel) and 1 h (right panel). (FIG. 9C) Quantitative analysis of salicylic acid level in plasma samples, unpaired Student's t test. UHPLC-Q-TOF/MS, ultra-high-performance liquid chromatography-quadrupole time-of-flight mass spectrometry.

Figure 10A:
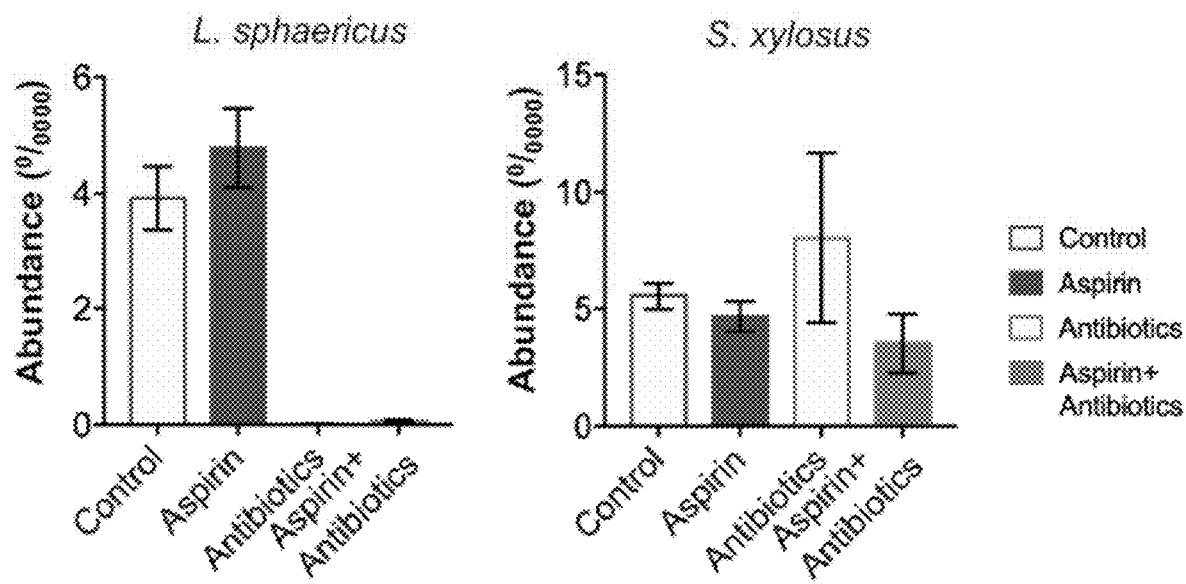
Figure 10B:
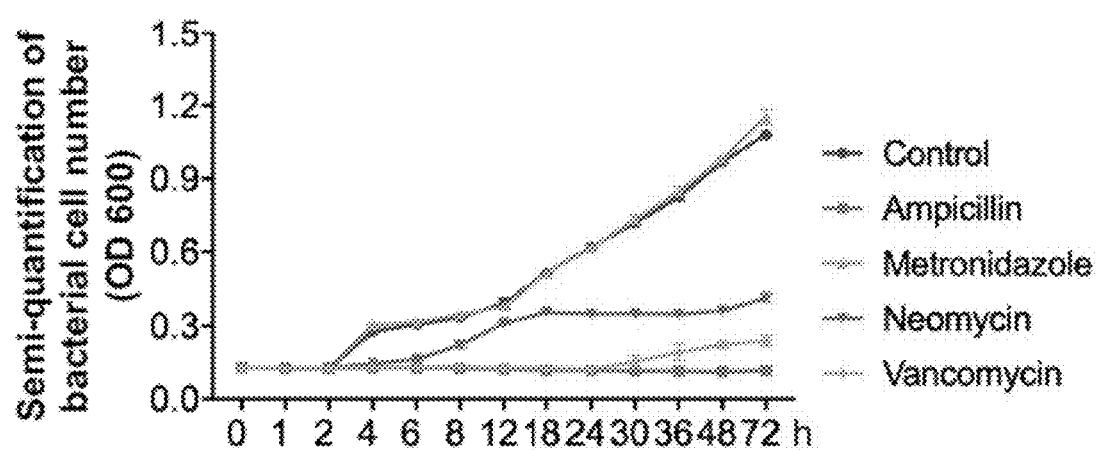

FIG. 10A-FIG. 10B. Ampicillin in antibiotics cocktail eradicates *Lysinibacillus sphaericus* in the gut. (FIG. 10A) Abundance of *L. sphaericus* and *S. xylosus* in fecal samples of mice with and without antibiotic treatment. (FIG. 10B) The impact of different antibiotics on cell growth of *L. sphaericus. L. sphaericus, Lysinibacillus sphaericus; S. xylosus, Staphylococcus xylosus*.

Figure 11A:
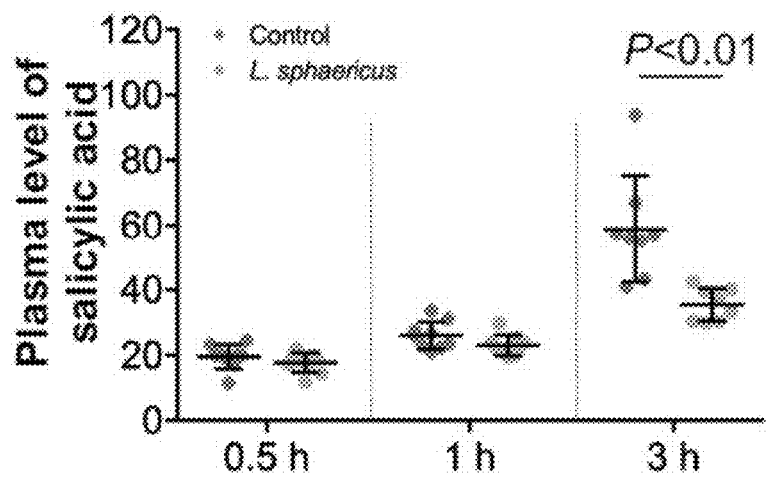
Figure 11B:
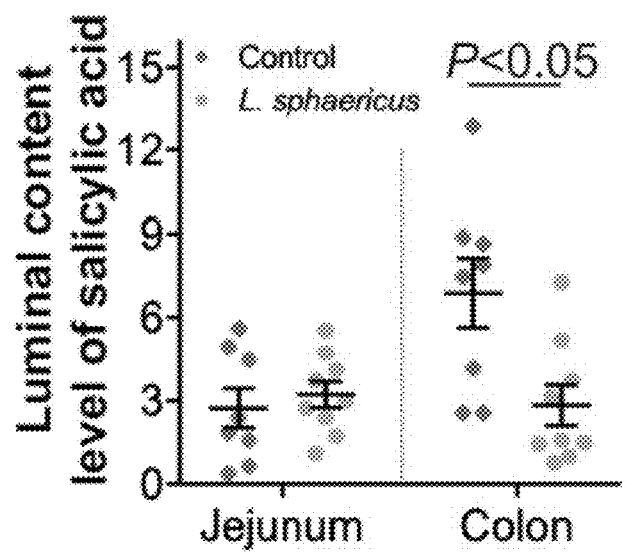

FIG. 11A-FIG. 11B. Salicylic acid level in plasma (FIG. 11A) and luminal contents (FIG. 11B), unpaired Student's t test.

DEFINITIONS

In this disclosure the terms "colorectal cancer (CRC)" and "colon cancer" have the same meaning and refer to a cancer of the large intestine (colon), the lower part of human digestive system, although rectal cancer often more specifically refers to a cancer of the last several inches of the colon, the rectum. A "colorectal cancer cell" is a colon epithelial cell possessing characteristics of colon cancer and encompasses a precancerous cell, which is in the early stages of conversion to a cancer cell or which is predisposed for conversion to a cancer cell. Such cells may exhibit one or more phenotypic traits characteristic of the cancerous cells.

"Aspirin," also known as acetylsalicylic acid (ASA), is a commonly used anti-inflammation drug. It's chemical structure is:

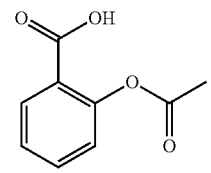

As used here, the term "aspirin-mediated chemoprotection against CRC" or any of its grammatical variations refers to a process in which individuals, such as those deemed to have heighted risk of developing CRC (e.g., with a family history of cancer, especially CRC, and/or other known risk factors), regardless of whether they have any clinical indication of early signs or precursors of CRC such colon polyps or cysts, are administered aspirin for the purpose of reducing their risk to develop CRC at a later time.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO01/12654, which may improve the stability (e.g., half-life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used herein, the term "gene expression" is used to refer to the transcription of a DNA to form an RNA molecule encoding a particular protein or the translation of a protein encoded by a polynucleotide sequence. In other words, both mRNA level and protein level encoded by a gene of interest are encompassed by the term "gene expression level" in this disclosure.

An "expression cassette" is a nucleic acid construct, generated recombinantly or synthetically, with a series of specified nucleic acid elements that permit transcription of a particular polynucleotide sequence in a host cell, for example, the transcription of an inhibitory RNA (e.g., such as miRNA or siRNA) or an anti-sense RNA targeting a specific, pre-selected sequence (e.g., a segment of the *Lysinibacillus sphaericus* genomic sequence). An expression cassette may be part of a plasmid, viral genome, or nucleic acid fragment. In other words, an expression cassette may be transferred or delivered as a part or/in the form of a bacterial plasmid or a viral vector or virus-like particle. Typically, an expression cassette includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. Other elements that may be present in an expression cassette include those that enhance transcription (e.g., enhancers) and terminate transcription (e.g., terminators), as well as those that confer certain binding affinity or antigenicity to the recombinant protein produced from the expression cassette.

As used in this application, an "increase" or a "decrease" refers to a detectable positive or negative change in quantity from a comparison control, e.g., an established standard control or cut-off value. An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, 1%, or even less variation from the standard control.

The term "inhibiting" or "inhibition," as used herein, refers to any detectable negative effect on a target biological process, such as RNA transcription, protein expression, cell proliferation, cellular signal transduction, cell proliferation, tumorigenicity, metastatic potential, and recurrence of a disease/condition. Typically, an inhibition is reflected in a decrease of at least 10%, 20%, 30%, 40%, or 50% in target process (e.g., level of a pertinent bacterium such as *Lysinibacillus sphaericus*; or the incidence of cancer occurrence such as CRC incidence) upon application of an inhibitor, when compared to a control where the inhibitor is not applied.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., a unique polynucleotide sequence from a pertinent bacterial species such as *Lysinibacillus sphaericus*. For example, "primers" can be used in a reverse-transcription polymerase chain reaction (RT-PCR) and quantitative polymerase chain reaction (qPCR) to quantify the gene expression. Typically at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. The primers used in particular embodiments are shown in Examples of the disclosure where their specific applications are indicated. In this disclosure the term "primer pair" means a pair of primers that hybridize to opposite strands a target DNA molecule or to regions of the target DNA which flank a nucleotide sequence to be amplified. In this disclosure the term "primer site", means the area of the target DNA or other nucleic acid to which a primer hybridizes.

The term "amount" or "level" as used in this application refers to the quantity of a bacterial species of interest, e.g., *Lysinibacillus sphaericus*, present in a sample. Such quantity may be expressed in the absolute terms, i.e., the total quantity of *Lysinibacillus sphaericus* in the sample, or in the relative terms, i.e., the percentage of *Lysinibacillus sphaericus* among all bacteria in the sample.

The term "treat" or "treating," as used in this application, describes to an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount" as used herein refers to an amount of a given substance that is sufficient in quantity to produce a desired effect. For example, an effective amount of an inhibitor of a specific bacterial species such as *Lysinibacillus sphaericus* is the amount of the inhibitor to achieve a decreased level (including to an undetectable level) of *Lysinibacillus sphaericus* in a recipient's gastrointestinal tract, e.g., as measured in a stool sample obtained from the recipient. As another example, an effective amount of aspirin is the amount of aspirin that, when administered to a patient, is able to achieve a detectable level of reduced risk of CRC in the patient. An amount adequate to achieve an intended effect in the therapeutic context is defined as the "therapeutically effective dose." The dosing range varies with the nature of the therapeutic agent being administered and other factors such as the route of administration and the severity of a patient's condition.

The term "anti-bacterial agent" refers to any substance that is capable of inhibiting, suppressing, eliminating, or preventing the growth or proliferation of a bacterial species, respectively, such as *Lysinibacillus sphaericus*. Known agents with anti-bacterial activity include various antibiotics that generally suppress the proliferation of a broad spectrum of bacterial species as well as agents such as antisense oligonucleotides, small inhibitory RNAs, and the like that can inhibit the proliferation of specific bacterial species.

"Percentage relative abundance," when used in the context of describing the presence of a particular bacterial species (e.g., *Lysinibacillus sphaericus*) in relation to all bacterial species, respectively, present in the same environment, refers to the relative amount of the bacterial species out of the amount of all bacterial species, respectively, as expressed in a percentage form. For instance, the percentage relative abundance of one particular bacterial species can be determined by comparing the quantity of DNA or RNA specific for this species (e.g., determined by quantitative polymerase chain reaction (PCR) including reverse transcription (RT)-PCR) in one given sample with the quantity of all bacterial DNA (e.g., determined by quantitative PCR including RT-PCR and sequencing based on 16S rRNA sequence) in the same sample.

"Absolute abundance," when used in the context of describing the presence of a particular bacterial species (e.g., *Lysinibacillus sphaericus*) in a sample (e.g., a stool sample taken from a test subject), refers to the amount of DNA derived from the bacterial species, respectively, out of the amount of all DNA in the sample. For instance, the absolute abundance of one bacterium can be determined by comparing the quantity of DNA specific for this bacterial species (e.g., determined by quantitative PCR including RT-PCR) in one given sample with the quantity of all DNA in the same sample.

"Total bacterial load" of a sample, as used herein, refers to the amount of all bacterial DNA, respectively, out of the amount of all DNA in the sample. For instance, the absolute abundance of bacteria can be determined by comparing the quantity of bacterial specific DNA (e.g., 16S rRNA determined by quantitative RT-PCR) in one given sample with the quantity of all DNA in the same sample.

The term "subject" or "subject in need of CRC chemoprotection," as used herein, includes individuals who seek medical attention due to risk of, or precursor symptoms of, colon cancer. Subjects or individuals in need of CRC chemoprotaction (such as by aspirin) include those with a genetic predisposition or family history for cancers especially colorectal cancer, those that have suffered relevant symptoms in the past, those that have been exposed to a triggering substance or event, as well as those suffering from chronic or acute symptoms that can act as the precursor or early indication of CRC. A "subject in need of CRC chemoprotection" may be any gender and at any age of life. In some cases, the subject may be a patient who has been diagnosed with symptoms that can overtime lead to or evolve into colorectal cancer (e.g., colon polyps or cysts).

"Inhibitors," "activators," and "modulators" of a pertinent bacterial species (such as *Lysinibacillus sphaericus*) refer to inhibitory, activating, or modulating molecules, respectively, identified using in vitro and in vivo assays for their capability to positively or negatively modulate the bacterium's proliferation or survival. The term "modulator" includes inhibitors and activators. Inhibitors are agents that, e.g., partially or totally block binding, decrease, prevent, delay activation, inactivate, desensitize, or down regulate the level or amount of the pertinent protein, potentially by suppressing downstream effects such as the growth or survival of the colorectal cancer cells. In some cases, the inhibitor directly or indirectly binds to a target DNA or RNA, such as an antisense molecule or micro RNA. Inhibitors, as used herein, are synonymous with inactivators and antagonists. Activators are agents that, e.g., stimulate, increase, facilitate, enhance activation, sensitize or up regulate the level or amount of a pertinent protein, potentially by promoting downstream effects such as the growth or survival of the colorectal cancer cells. Inhibitors, activators, and modulators can be macromolecules such as polynucleotides, polypeptides including antibodies and antibody fragments, or they can be small molecules including carbohydrate-containing molecules, siRNAs, RNA aptamers, and the like.

As used herein, the term "about" denotes a range of value encompassing +/-10% of a pre-determined value. For instance, "about 10" means 9 to 11.

In this disclosure the term "or" is generally employed in its sense including "and/or" unless the content clearly dictates otherwise.

DETAILED DESCRIPTION OF THE INVENTION

I. Introduction

The subject matter disclosed herein generally relates to methods for assessing effectiveness in aspirin-mediated chemoproteciont against colorectal cancer in patients as well as methods for improving effectiveness of aspirin-mediated chemoprotection against colorectal cancer in patients.

Gut microbiota is important in colorectal cancer (CRC) and drug metabolism. This study was intended to determine the role of gut microbiota in aspirin-mediated chemoprevention of CRC in experimental animal models.

Azoxymethane and dextran sulfate sodium (AOM/DSS) treated and APC$^{min/+}$ mice were administered aspirin with or without antibiotics. Germ-free mice were used for validation. Arylesterase activity assay, liquid chromatography/mass spectrometry, and 16S rRNA gene sequencing were used to identify the microbes that degrade aspirin.

Aspirin reduced colorectal tumor number and load in AOM/DSS-treated mice and in APC$^{min/+}$ mice with depleted microbiota, but not in mice with intact microbiota. Consistently, decreased tumorigenesis were observed in aspirin-treated germ-free mice but not in conventionalized germ-free mice. Plasma aspirin levels were higher in microbiota-depleted mice than microbiota-intact mice. In vitro experiments revealed that gut microbiota possessed aspirin-degradation ability and identified *Lysinibacillus sphaericus* as a key microbe in aspirin degradation. Furthermore, *L. sphaericus*-monocolonized germ-free mice showed decreased plasma aspirin levels relative to control mice, confirming the role of this bacterium in reducing aspirin bioavailability. Aspirin-mediated CRC chemoprevention was observed with increased aspirin dosage in conventional mice, but dampened by increasing the abundance of *L. sphaericus*. Moreover, aspirin modulates gut microbiota by enrichment of *Bifidobacterium* and *Lactobacillus*.

Thus, this study provide evidence demonstrating that gut microbiota impacts the chemopreventive efficacy of aspirin on CRC by modulating aspirin bioavailability in mice. *L. sphaericus* plays a role in aspirin degradation and thereby impairs the CRC preventive efficacy by aspirin. Aspirin treatment leads to enrichment of gut probiotics, which may contribute to its CRC protective effect.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of interest used in this invention, e.g., the polynucleotide sequence of a DNA or RNA unique to a bacterial species of interest (such as *L. sphaericus*), and synthetic oligonucleotides (e.g., primers) can be verified using methods well-known in the pertinent research field, for example, the chain termination method for double-stranded templates of Wallace et al., *Gene* 16: 21-26 (1981).

III. Sample Acquisition and Analysis

The present invention relates to detecting qualitatively and/or quantitatively (e.g., determining the presence or absence of and/or measuring the level or amount of) a specific bacterium *Lysinibacillus sphaericus* found in a sample taken from the gastrointestinal tract of a patient being tested, for example, a stool sample, as a means to determine the likelihood of effective aspirin-mediated chemoprotection against the risk of colorectal cancer in the patient. Thus, the first steps of practicing this invention are to obtain a sample such as a stool sample from a test subject and extract bacterial polynucleotide sequences from the sample.

A. Acquisition and Preparation of Samples

A sample for the gastrointestinal tract is obtained from a person to be tested or monitored for treatment effectiveness or survival. Stool samples are typically used. Collection of such samples is typically carried out either in patient's home or in a clinic/doctor's office. After being obtained, the samples may be stored according to standard procedures prior to further preparation. The analysis of DNA or RNA found in a patient's sample according to the present invention may be performed using established techniques. The methods for preparing the samples for nucleic acid extraction are well-known among those of skill in the art and described herein.

B. Extraction and Quantitation of DNA and RNA

Methods for extracting DNA and RNA from a biological sample are well known and routinely practiced in the art of molecular biology, see, e.g., Sambrook and Russell, supra. For DNA analysis, RNA contamination should be eliminated to avoid interference with DNA analysis. Once DNA is extracted from a sample, the presence and amount of any particular DNA species, such as DNA sequence unique to *Lysinibacillus sphaericus*, may be determined and quantified. The preferred method for determining the DNA level is an amplification-based method, e.g., by polymerase chain reaction (PCR), including quantitative polymerase chain reaction (qPCR) for RNA quantitative analysis.

For RNA analysis, the general methods of RNA preparation can be followed, see, e.g., Sambrook and Russell, supra; various commercially available reagents or kits, such as Trizol reagent (Invitrogen, Carlsbad, Calif.), RNeasy Mini Kits (Qiagen, Hilden, Germany), miRNeasy FFPE Kit (Qiagen, Hilden, Germany) and PolyATtract® Series 9600™ (Promega, Madison, Wis.), may also be used to obtain mRNA from a biological sample from a test subject. Combinations of more than one of these methods may also be used. It is essential that all contaminating DNA be eliminated from the RNA preparations. Thus, careful handling of the samples, thorough treatment with DNase, and proper negative controls in the amplification and quantification steps should be used.

Once mRNA is extracted from a sample, the amount of any particular RNA species, such as 16S rRNA, may be quantified. The preferred method for determining the miRNA level is an amplification-based method, e.g., by polymerase chain reaction (PCR), including reverse transcription-polymerase chain reaction (RT-PCR) and quantitative polymerase chain reaction (qPCR) for RNA quantitative analysis.

Prior to amplification, miRNA must be first reverse transcribed: a DNA copy (cDNA) of the target RNA must be synthesized. This is achieved by reverse transcription, which can be carried out using a reverse transcription primer specific for the *Lysinibacillus sphaericus* 16S rRNA in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well-known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

IV. Aspirin Chemoprotection Against Colorectal Cancer

By illustrating the inverse correlation of *Lysinibacillus sphaericus* level or relative abundance in a subject's gastrointestinal tract and his likelihood of achieving desirable clinical outcome or protective effects from aspirin administration for the purpose of chemoprotection against CRC, especially that the presence or increased *Lysinibacillus sphaericus* level or relative abundance can diminish or even eliminate the chemoprotective effects from aspirin administration to the subject, the present invention provides a novel treatment method for improving aspirin's protective efficacy in an individual against colorectal cancer, in particular those who have known risk factors for later developing CRC, such as family history of cancer, especially CRC, colon polyps or cysts, etc. A patient who has been prescribed by his physician to receive aspirin administration for chemoprotection against CRC may, just prior (e.g., 1, 2, 3, 4, 5, 6, or up to 7 days prior) to the start of aspirin administration or at the same time of aspirin administration, receive treatment to suppress the level or relative abundance, up to eliminate the presence, of *Lysinibacillus sphaericus* in his gastrointestinal tract, such that colorectal epithelial cells can be sensitized and become more receptive to the chemoprotective agent such as aspirin, allowing the subsequent or concurrent aspirin administration to yield more favorable clinical outcome. The treatment for suppressing the level or relative abundance (up to eliminating the presence) of *Lysinibacillus sphaericus* may concur the entire duration of aspirin administration.

Patients receiving such pre-treatment or concurrent treatment for suppressing the level or relative abundance of *Lysinibacillus sphaericus* may be measured to detect the presence and/or level of *L. sphaericus* before, during, and after the aspirin treatment to monitor efficacy of aspirin-mediated chemoprotection. Patients suitable for such combination treatment may include those who inherently have high level of *Lysinibacillus sphaericus* in their stool samples or gastrointestinal tract and who have been deemed, according the assessment methods of this invention, unlikely to benefit from aspirin administration for chemoprotection against CRC. Once their *Lysinibacillus sphaericus* level is lower, especially when becoming undetectable, due to the treatment suppressing *Lysinibacillus sphaericus*, they may become appropriate candidates for the aspirin-based chemoprotection who are likely to achieve desirable clinical outcome and therefore should be prescribed aspirin administration for reducing the risk of CRC.

Various methods can be employed to suppress the level or relative abundance of *Lysinibacillus sphaericus*, permanently or temporarily. An expression cassette encoding a polynucleotide sequence for inhibiting expression of key gene or genes of *Lysinibacillus sphaericus* (e.g., small inhibitory RNA such as miRNA or antisense RNA) may be used for this purpose. Typically, such an expression cassette has a promoter directing the transcription of the coding sequence, preferably a tissue-specific promoter directing transcription in the colorectal mucosal tissue, so as to ensure adequate expression of the inhibitory RNA in the colorectal epithelial cells. In some embodiments, the expression cassette may be contained within a viral vector or as a part of a virus-like particle that can readily transfect into a target tissue or cell.

An expression cassette for the expression of an inhibitory polynucleotide sequence targeting one or more *Lysinibacillus sphaericus* genes can be administered directly to the target tissue by injection, e.g., oral ingestion, or by suppository to the colorectal segment of the digestive tract. One possibility of delivery is via liposomes, which serve to target it to a particular tissue, as well as increase the half-life of the composition. Liposomes include emulsions, foams, micelles, insoluble monolayers, liquid crystals, phospholipid dispersions, lamellar layers and the like. In these preparations the expression cassette to be delivered is incorporated as part of a liposome, alone or in conjunction with a molecule which binds to, e.g., a receptor prevalent among the targeted cells, or with other therapeutic or immunogenic compositions. Formulation for administration by oral, rectal, or other means is contemplated.

V. Kits

The invention provides compositions and kits for practicing the methods described herein to detect the presence and/or assess the level or relative abundance of *Lysinibacillus sphaericus* in a sample, such as a stool sample, obtained from a subject. For example, the presence and/or level or relative abundance of *Lysinibacillus sphaericus* is determined in a fecal sample taken from a patient, such that the patient may have been treated accordingly, e.g., if the patient is deemed likely to respond positively to aspirin treatment as chemoprotection against CRC, the patient will be given the treatment; otherwise the patient will not be given aspirin treatment but an alternative treatment as a meaning of chemoprotection against CRC, or the patient may be given aspirin treatment only after he is first given an additional treatment to suppress the level or relative abundance (up to reducing it to an undetectable level) of *Lysinibacillus sphaericus* in his gastrointestinal tract (for example, administration of an expression cassette such as one contained in a viral vector directing the expression of an inhibitory RNA molecule, especially in colorectal tissue to inhibit the expression of one or more genes of *Lysinibacillus sphaericus*). In the case of assessing likely efficacy from aspirin administration as a means for chemoprotection against CRC, a patient who has a higher level or relative abundance of *Lysinibacillus sphaericus* in his stool sample is deemed to have a lower chance to benefit from the aspirin administration against CRC risk than another patient who has a higher level or relative abundance of *Lysinibacillus sphaericus* in his stool sample. For example, a first patient who has a detectable level of *L. sphaericus* in his stool sample is deemed unlikely to receive effective chemoprotection against CRC from aspirin administration, who may not receive aspirin treatment (rather using an alternative chemoprotection method) or may start aspirin treatment shortly after or at the same time of receiving treatment to suppress or eliminate *Lysinibacillus sphaericus* in his gastrointestinal tract; whereas a second patient who has no detectable level *L. sphaericus* in her stool sample is deemed likely to benefit from effective chemoprotection against CRC from aspirin administration, who may immediately start aspirin treatment. Thus, a first patient who has a detectable level of *L. sphaericus* in his stool sample is deemed to have a lower likelihood of achieving effective chemoprotection against CRC from aspirin administration than a second patient who has no detectable level *L. sphaericus* in his stool sample.

In some embodiments, kits for carrying out assays for detecting the presence and/or for determining the level or relative abundance of *Lysinibacillus sphaericus* typically include reagents useful for carrying out an RT-PCR for the qualitative and/or quantitative determination of a polynucleotide sequence such as 16S rRNA unique to the bacterium: at least one oligonucleotide useful for reverse transcription and at least one set of three oligonucleotide primers for PCR to amplify the unique polynucleotide sequence. In some cases, one or more of the oligonucleotides may be labeled with a detectable moiety. In some cases, a hydrolysis probe is included in the kit to allow instant quantitative measure of amplification product. Typically, the hydrolysis probe has a fluorescent label and a quencher. The Examples section of this disclosure provides some examples of such primers and probes.

Typically, the kits also include positive and negative controls for the specific assay method. In addition, the kits of this invention may provide instruction manuals to guide users in analyzing samples and assessing the likelihood of effective chemoprotection against CRC by aspirin treatment in a test subject.

In a further aspect, the present invention can also be embodied in a device or a system comprising one or more such devices, which is capable of carrying out all or some of the method steps described herein. For instance, in some cases, the device or system performs the following steps upon receiving a first sample (e.g., a fecal sample) from a first test subject and a second sample of the same type from a second test subject to assess their relative likelihood of achieving effective chemoprotection against CRC by aspirin treatment: (a) determining in the sample the level or relative abundance of *Lysinibacillus sphaericus* (e.g., based on its unique 16S rRNA sequence); (b) comparing the relative amount/level with a second relative amount/level obtained from a second sample of the same type taken from a second test subject; and (c) providing an output indicating whether the first test subject is likely to benefit from chemoprotection against CRC by aspirin treatment and therefore should immediately receive such treatment or whether the first test subject is more likely than the second test subject to benefit from chemoprotection against CRC by aspirin treatment. In some cases, the device or system of the invention performs the task of steps (b) and (c), after step (a) has been performed and the amount or concentration from step (a) has been entered into the device.

In one example, the device or system performs the following steps upon receiving a sample (e.g., a fecal sample) from a test subject to assess the likelihood of achieving effective chemoprotection against CRC by aspirin treatment: (a) determining in the sample the presence or absence of *Lysinibacillus sphaericus* (e.g., based on its unique 16S rRNA sequence); (b) determining the test subject as likely to achieve effective chemoprotection against CRC by aspirin treatment when *Lysinibacillus sphaericus* is absent in the sample, and determining the test subject as unlikely to achieve effective chemoprotection against CRC by aspirin treatment when *Lysinibacillus sphaericus* is present in the sample; and (c) providing an output indicating whether the test subject should immediately receive aspirin treatment or whether the test subject should use alternative means of chemoprotection against CRC other than aspirin treatment or should receive pre-treatment or concurrent treatment to suppress or eliminate *Lysinibacillus sphaericus* from his gastrointestinal tract before starting aspirin administration. In some cases, the device or system of the invention performs the task of steps (b) and (c), after step (a) has been performed and the presence or absence of *Lysinibacillus sphaericus* from step (a) has been entered into the device.

Preferably, the device or system of this invention is partially or fully automated.

EXAMPLES

The following examples are provided by way of illustration only and not by way of limitation. Those of skill in the art will readily recognize a variety of non-critical parameters that could be changed or modified to yield essentially the same or similar results.

Example 1: Gut Microbiota Modulates the Chemopreventive Efficacy of Aspirin on Colorectal Cancer Through Reducing Aspirin Bioavailability Introduction Colorectal cancer (CRC) incidence remains high globally despite efforts devoted towards its control. The global persistence of CRC necessitates a paradigm shift in its management strategy, from clinical treatment to preclinical prevention[1]. Aspirin has emerged as a promising agent for chemoprevention of colorectal adenoma and cancer. The mechanistic basis for the preventive effect of aspirin is presumed to be the irreversible inhibition of cyclooxygenase-2 (COX-2) and the consequent downregulation of prostaglandin E2 (PGE2)[2,3]. Accumulating evidence from clinical randomized control trials consistently highlighted the effectiveness of aspirin on CRC prevention[4-6]. The United States Preventive Services Task Force (USPSTF) has recommended long-term aspirin use for CRC prevention among the population primarily selected for cardiovascular disease prevention[7]. Nevertheless, with largely unknown reasons, the chemopreventive efficacy of aspirin varies among individuals[8,9].

CRC is distinct from other cancer types due to its direct exposure to trillions of gut microorganisms during development. The gut microbiota have been identified by researchers as an important factor in colorectal cancer initiation and progression[10-13]. Notably, the composition of the gut microbiota is responsive to multiple host factors including diet[14], life style[15,16], and medications[17,18]. Drugs including aspirin can alter the composition of microbiota in the oral cavity of rats and the gut of human[19,20].

Interaction between drugs and microbiota can be bidirectional, including drug-induced shift in microbial composition and microbiota-mediated modulation of drug potency[21]. The biological transformation of drugs by the gut microbiota can contribute to the activation[22], inactivation[23], or mediation of their therapeutic efficacy[18]. A recent study indicated that gut microbiota reduced the antithrombotic activity of aspirin by reducing its level in circulation after oral administration[24]. Moreover, the difference in blood levels of aspirin in rats with and without microbial depletion was abolished by intravenous administration of aspirin[24]. These findings provide clues for the existence of crosstalk between aspirin and the gut microbiota. However, the impact of such crosstalk on CRC chemoprevention remains unexplored.

This study was performed to delineate the role of gut microbiota in aspirin-mediated CRC chemoprevention. The present inventors examined the impact of microbiota depletion on the preventive efficacy of aspirin in two conventional CRC mouse models and validated the findings in germ-free mice. The potential gut microbes that can modulate the chemopreventive efficacy of aspirin on CRC were then screened, identified, and characterized.

Materials and Methods

Conventional Mouse Models

Male C57BL/6 mice at 8 weeks old were intraperitoneally injected with 10 mg/kg azoxymethane (AOM) (Merck, Darmstadt, Germany), followed by 3 cycles of dextran sulfate sodium (DSS) (MP Biomedicals, Solon, Ohio) administration to mimic colitis-associated CRC. For each cycle, mice were allowed free access to drinking water supplemented with 2.0% DSS for 5 days, followed by 16 days of regular water.

Drinking water was supplemented with antibiotics cocktail (0.2 g/L of ampicillin, neomycin and metronidazole and 0.1 g/L of vancomycin) for two weeks, every other two weeks, till the end of experiment, to deplete the gut microbiota. Aspirin (Byer, Leverkusen, Germany), freshly prepared (400 mg/L) in drinking water twice a week, was continuously given to mice through the entire experiment. Male APC$^{min/+}$ C57BL/6 mice at 5 to 6 weeks old were exposed to the same antibiotics and aspirin treatments as AOM/DSS mouse model to mimic spontaneous genetically induced CRC.

At day 80 for AOM/DSS model and day 84 for APC$^{min/+}$ model, mice were harvested. The intestines were longitudinally opened along the mesenteric margin and flushed with ice-cold phosphate-buffered saline (PBS). Solid neoplastic lesions were carefully counted for tumor number and measured for tumor size (average diameter, (major diameter+ minor diameter)/2) and tumor load (sum of average diameters of all tumors). The intestinal tissues were fixed in 10% neutral buffered formalin and embedded in paraffin. Sections (4 μm) were stained with hematoxylin and eosin for histological examination by a pathologist (A/Professor Anthony W H Chan) who was blind to the experimental design. The remaining tissues were snap-frozen in liquid nitrogen, and stored at −80° C. until use. All procedures adhered to the guidelines approved by the Animal Experimentation Ethics Committee of the Chinese University of Hong Kong.

Germ-Free Mouse Models

Germ-free wild-type Kunming mice (10 weeks old) in male gender were treated with AOM and DSS to induce intestinal neoplasia. The treatment regimens of AOM, DSS and aspirin were the same as described for conventional mice. In a separate experiment, to determine the direct effects of microbiota on chemoprevention, germ-free mice were conventionalized after their cages were placed out of germ-free environment at 10 weeks old prior to treatment. The remaining procedures performed were the same as described for conventional mice. Germ-free mice were bred at the Department of Laboratory Animal Science, The Third Military Medical University, Chongqing, China. The germ-free animal experiments were approved by the Animal Experimentation Ethics Committee of The Third Military Medical University.

Fecal DNA Extraction and Bacterial Load Quantification

Fecal DNA was extracted using Fecal DNA MiniPrep kit (Zymo research, Irvine, Calif.). The quality and quantity of DNA were determined by NanoDrop2000 spectrophotometer (Thermo Fisher Scientific, Waltham, Mass.). Bacterial load was calculated by qPCR analysis of the relative 16S rRNA gene with normalization by stool weight. qPCR was performed using ROX Reference Dye II and TB Green Premix Ex Tac (both from Takara, Shiga, Japan) in the QuantStudio 7 Flex system (Thermo Fisher Scientific). The primers for amplification of the universal 16S rRNA gene were 5'-ACTCCTACGGGAGGCAGCAGT-3' (SEQ ID NO:1) and 5'-ATTACCGCGGCTGCTGGC-3' (SEQ ID NO:2).

Quantitative Reverse-Transcription PCR (qRT-PCR)

Total RNA in distal colonic tissues was extracted using TRIzol reagent (Thermo Fisher Scientific). The quality and quantity of RNA were determined by NanoDrop2000 spectrophotometer. Complementary DNA (cDNA) was synthesized from 1000 ng of the extracted RNA by reverse transcription (PrimeScript RT Reagent Kit with gDNA Eraser) (Takara, Japan) and analyzed by qPCR with normalization by GAPDH. The primers used were:

```
COX-2
(5'-TGCTGGAAAAGGTTCTTCTACGG-3' (SEQ ID NO: 3)
and

5'-GAACCCAGGTCCTCGCTTATG-3' (SEQ ID NO: 4)
and

GAPDH
(5'-GCATGGCCTTCCGTGTTC-3' (SEQ ID NO: 5)
and

5'-GATGTCATCATACTTGGCAGGTTT-3' (SEQ ID NO: 6).
```

Measurement of PGE2 by Enzyme-Linked Immunosorbent Assay (ELISA)

The plasma levels of PGE2 were measured using Multispecies Competitive ELISA Kit (Thermo Fisher Scientific). Briefly, 500 μL ice-cold methanol was added to 150 μL of plasma sample with 28 μM indomethacin and mixed vigorously. After acidification by 2M HCl to pH 3.5, the aqueous layer was extracted with 500 μL chloroform and centrifuged at 2000 g for 20 min[25]. The upper-layer organic phase was discarded, and the remaining aqueous phase was evaporated to dryness under nitrogen, before measurement by the kit.

Aspirin Assay

The levels of aspirin from plasma, gut luminal contents and culture medium was determined by ultra-high-performance liquid chromatography-quadrupole time-of-flight mass spectrometry (UHPLC-Q-TOF/MS). The detection sample was mixed in 5 μL 4-C1-phenylalanine (0.39 mg/mL, internal standard). Aspirin and salicylic acid were extracted twice by 400 μL cold methanol. Supernatants were dried under nitrogen stream and detected by UHPLC (1290 Infinity LC, Agilent, Santa Clara, Calif.) and MS (6550 Q-TOF/MS, Agilent, CA).

Salicylic Acid Assay

The primary metabolite of aspirin, salicylic acid, in culture medium was examined by Trinder's method[26]. Equal number of fecal bacteria (estimated by optical density (OD) 600) from APC$^{min/+}$ mice with and without antibiotic treatment were inoculated into the brain heart infusion (BHI) medium (Thermo Fisher Scientific) containing aspirin (10 mM). After 2-hour co-incubation at 37° C., the level of salicylic acid in medium was measured by Trinder's method[26]. Briefly, the supernatant of medium was mixed with a solution containing 40 g ferric nitrate, 40 g mercuric chloride and 120 mL 1N HCL in 1 L ddH$_2$O at 1:5 ratio. Salicylic acid was quantified by absorbance value at 540 nm. The plasma and luminal content levels of salicylic acid were evaluated by UHPLC-Q-TOF/MS.

Fecal Bacteria Culture

Mouse feces were mixed with cooked meat (CM) medium (Thermo Fisher Scientific). The fecal commensal bacteria were cultured aerobically in the incubator (IB-01E, Jeio Tech, Kyunggi-Do, Korea) and anaerobically in anaerobic chamber (Bactron300-2, Sheldon Manufacturing, Cornelius, Oreg.) at 37° C. for 48 h. For anaerobic culture, the medium in containers with loosened caps was deoxygenated by heat and immediately transferred into anaerobic chamber at least three days before use.

Arylesterase Activity Assay

Arylesterase activity, depicting the degradation of aspirin, in conditional bacterial culture medium (CM) was determined by hydrolysis of p-nitrophenyl acetate (Merck, Darmstadt, Germany), a chemical with similar structure with aspirin. The reaction solution containing 10 μL of supernatant and 190 μL of 0.35 mmol/L p-nitrophenyl acetate was prepared in 96-well plates. Arylesterase activity in each well was determined by absorbance at 405 nm using spectrophotometer (Thermo Fisher Scientific).

Screening of Fecal Bacteria by High-Throughput Arylesterase Assay

Fecal bacteria, from antibiotics-naive aspirin-treated $APC^{min/+}$ mice, cultured in CM medium were diluted and spread on BHI agar plates. Each colony was picked up after 48 h of aerobic culture at 37° C. and transferred respectively into one well of 96-well plates containing 150 μL BHI broth. After aerobic incubation at 37° C. for 48 h, the arylesterase activity of each well was measured and bacteria in the wells showing high arylesterase activity were sub-cultured in BHI broths for further analysis.

Metagenomic Sequencing Analysis of Fecal Samples

Whole-genome shotgun metagenomic sequencing of fecal samples from mice were performed on Illumina HiSeq 2000 (Illumina, San Diego, Calif.) as previously described[27]. Any adapter sequences in paired-end reads were clipped by checking for simple and palindromic matches of 10 and 30 bases with a library of universal ILLUmina Nextera, and Truseq adapter sequences if an adapter-read pair had a mismatch count of 2 or less. Mammalian genomes (hg38, felCat8, canFam3, mm10, rn6, susScr3, galGal4 and bosTau8; UCSC Genome Browser) and 6877 bacterial plasmids (NCBI RefSeq database accessed on May 12, 2016), 2116 complete plastomes (NCBI RefSeq database accessed on May 12, 2016) and 6093 UNiVec sequences (NCBI RefSeq database accessed on May 12, 2016), which are potential habitat-/laboratory-associated or extra-chromosomal sequence contaminants, were removed after alignment using Bowtie2 v_2.2.9 with "very-sensitive" default settings. Taxonomy was assigned to metagenomic reads using k-mer-based algorithms implemented in Kraken taxonomic annotation pipeline with each k-mer in a read mapped to the lowest common ancestor of all reference genomes with exact k-mer matches. Each query was thereafter classified to a taxon with the highest total hits of k-mer matched by pruning the general taxonomic trees affiliated with mapped genomes. The final metagenomic read counts were rarified to the sample with the lowest value and further normalized by cumulative sum scaling. In-house fecal metagenomic sequences were examined for the abundance of candidate bacteria identified from mouse fecal samples[27,28].

Identification and Validation of Bacteria with Aspirin-Degradation Effect

Bacteria, with high arylesterase activity, isolated from antibiotics-naive aspirin-treated $APC^{min/+}$ mice, were identified by matrix-assisted laser desorption/ionization time of flight mass spectrometry (MALDI-TOF/MS) using Microflex LT (Bruker, Karlsruhe, Germany). To confirm the identity of bacterial candidates, PCR-based amplification of bacterial 16S rRNA gene followed by sequencing was performed. The primers used amplification reactions were 27FYM (5'-AGAGTTTGATYMTGGCTCAG-3' (SEQ ID NO:7)) and 1492R (5'-GGTTACCTTGTTACGACTT3' (SEQ ID NO:8))[29]. Aspirin-degradation effect of the identified bacterial species was validated by measurement of the remaining aspirin level in aspirin-containing medium after 2-hour aerobic co-incubation with the identified bacteria.

Statistical Analysis

The numerical variables between 2 groups were compared using unpaired Student's t test or Mann-Whitney U test where appropriate. Comparisons of categorical variables between 2 groups were performed using Chi-square test or Fisher's exact test. Repeated measurement data were analyzed by two-way ANOVA test. All statistical analyses were conducted using GraphPad Prism, version 7.0 (GraphPad, La Jolla, Calif.) or SPSS, version 23.0 (IBM Corp., Armonk, N.Y.). Differences were considered significant if P values were less than 0.05.

Results

Figure 1B:
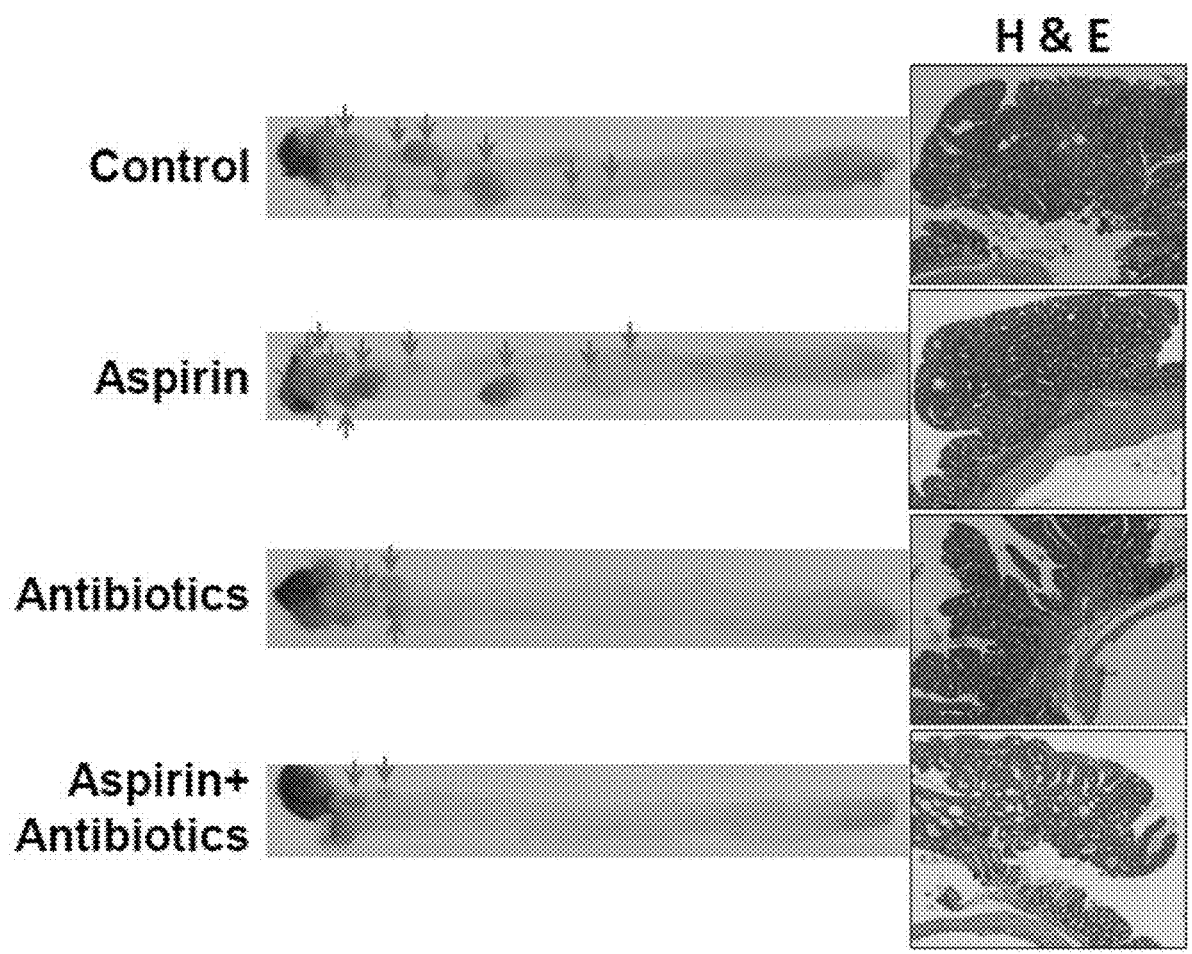
Figure 1C:
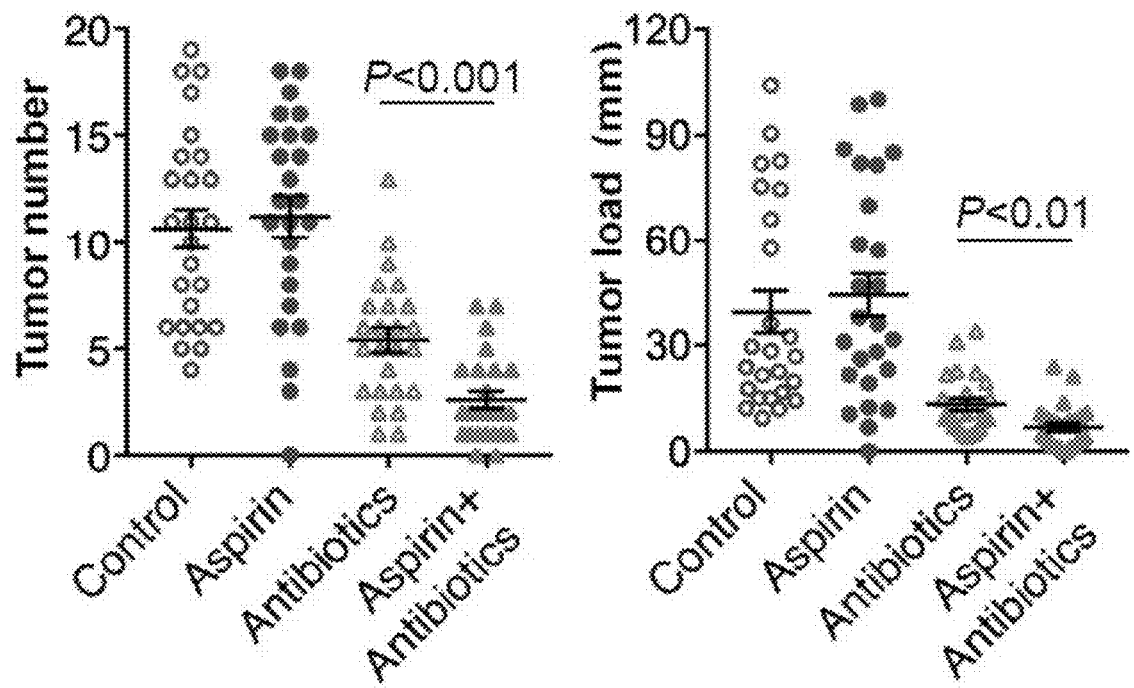
Figure 1D:
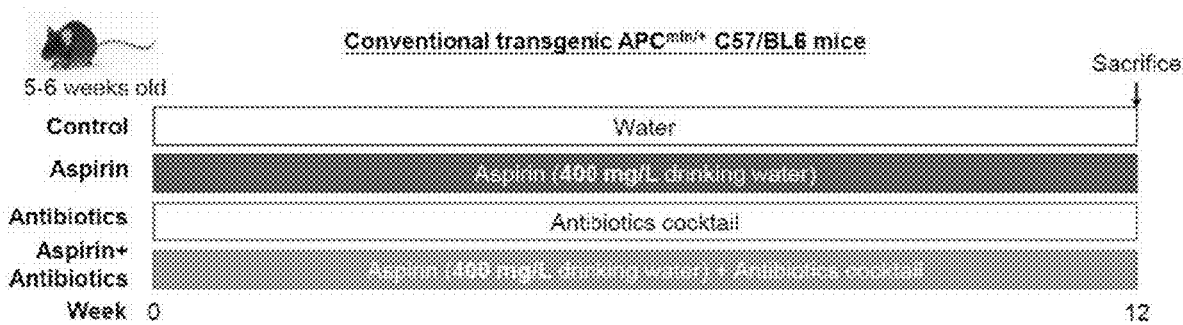
Figure 1E:
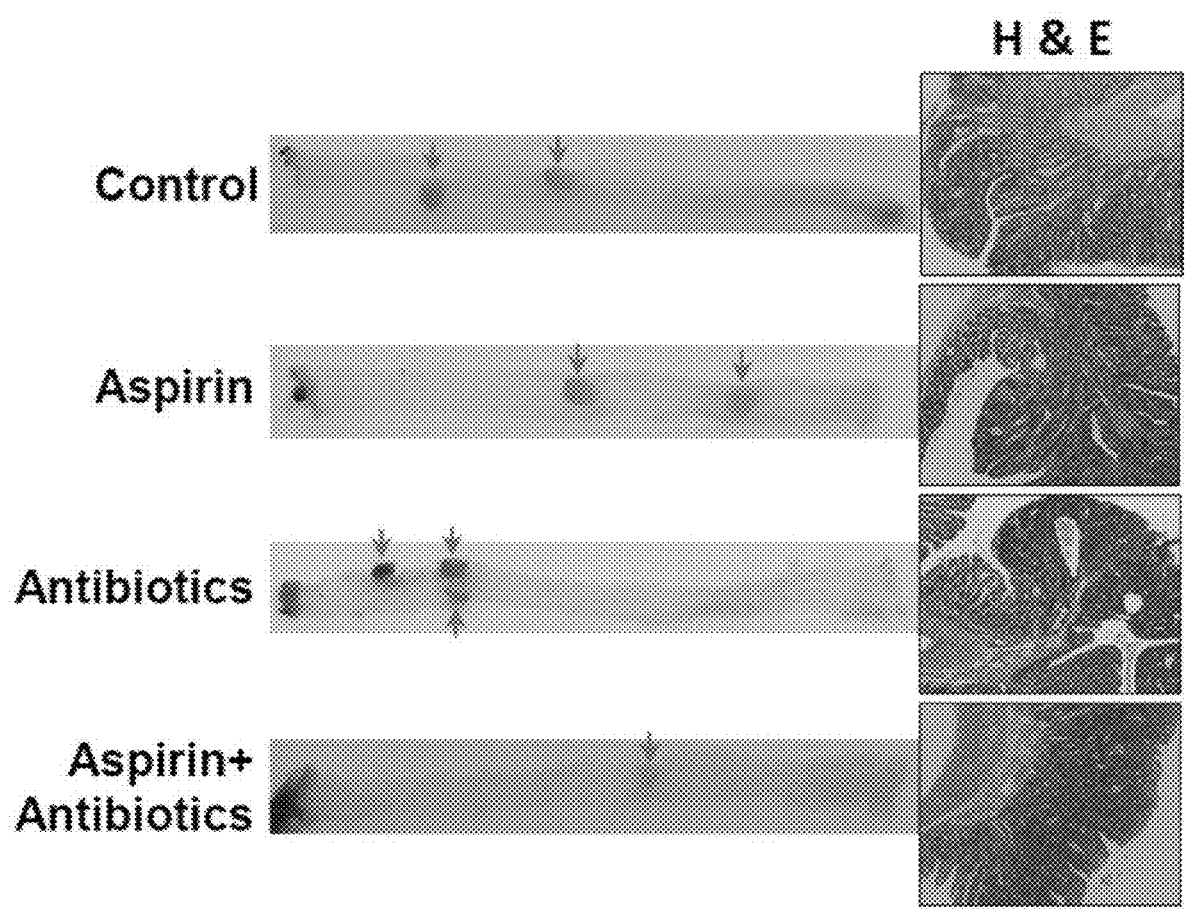
Figure 1F:
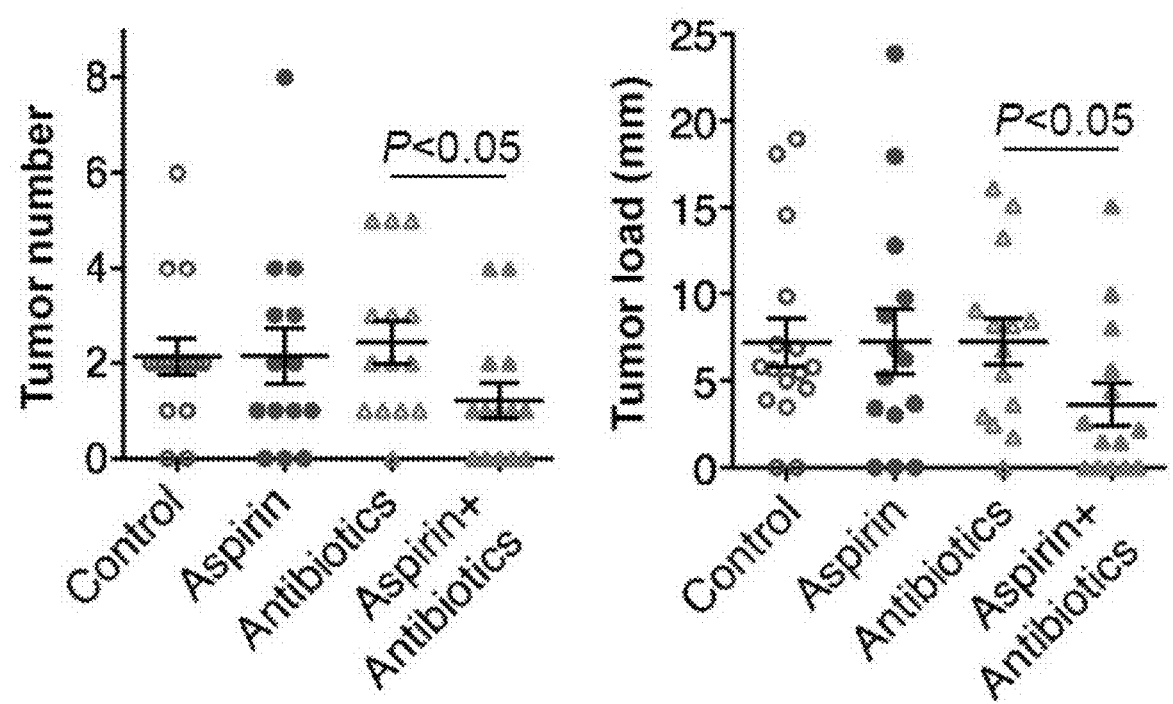

Depletion of Gut Microbiota Enhances the Effectiveness of Aspirin on CRC Prevention in Mice To evaluate the impact of gut microbiota on the chemoprevention of CRC by aspirin, antibiotics cocktail was used to deplete the gut microbiota in AOM/DSS-treated C57BL6 wildtype mice receiving aspirin (400 mg/L drinking water) (FIG. 1A). The successful depletion of gut bacteria by antibiotics was confirmed by quantification of fecal 16S rRNA levels (FIG. 8). Aspirin treatment led to significant reductions of colorectal tumor number and load in mice with microbiota-depleted mice, but not in mice with intact gut microbiota (FIGS. 1B and C). To verify this finding, another CRC model with transgenic $APC^{min/+}$ mice was established (FIG. 1D). Consistent with the results in AOM/DSS-induced CRC model, aspirin significantly decreased colorectal tumor number and load in microbiota-depleted $APC^{min/+}$ mice, but not in microbiota-intact controls (FIGS. 1E and F). These findings consistently indicate that the gut microbiota impairs the chemopreventive effect of aspirin on colorectal tumorigenesis.

Figure 2A:
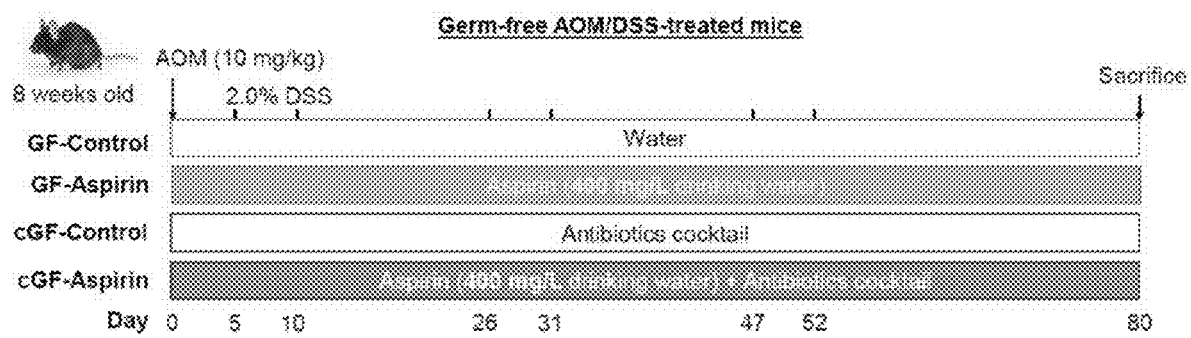
Figure 2B:
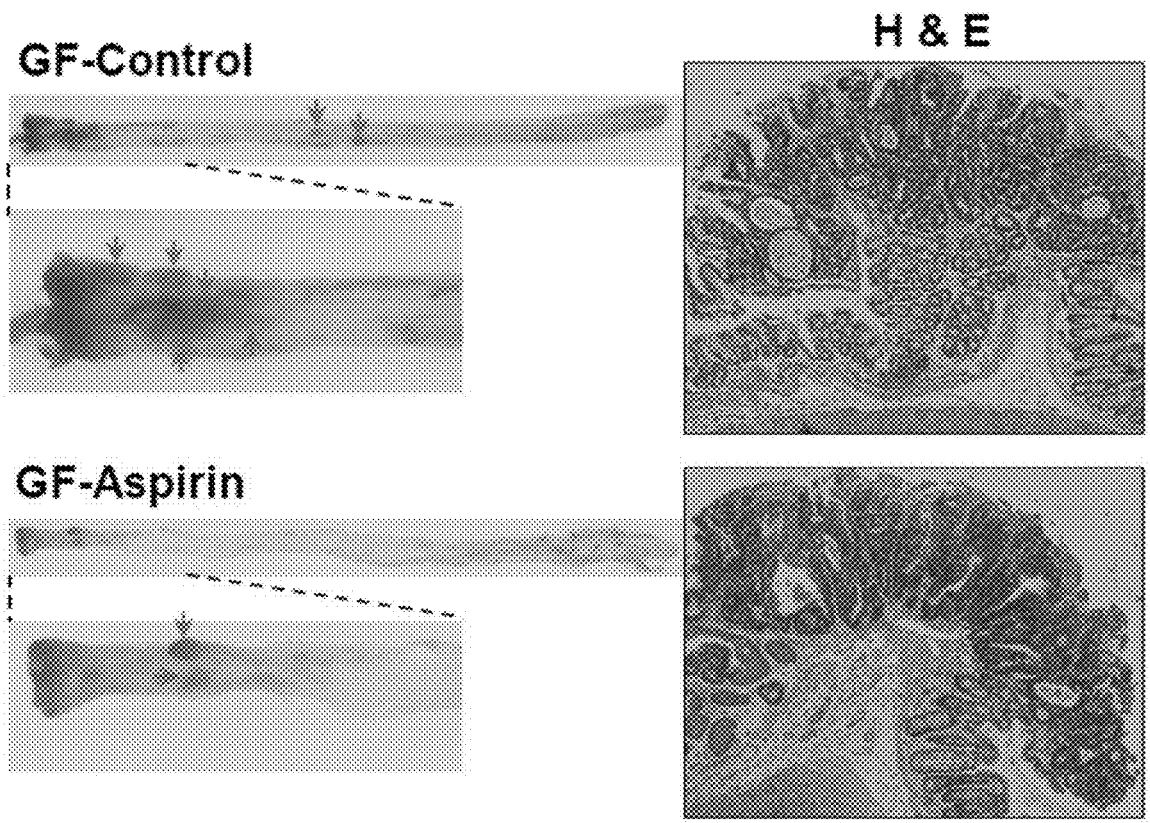
Figure 2C:
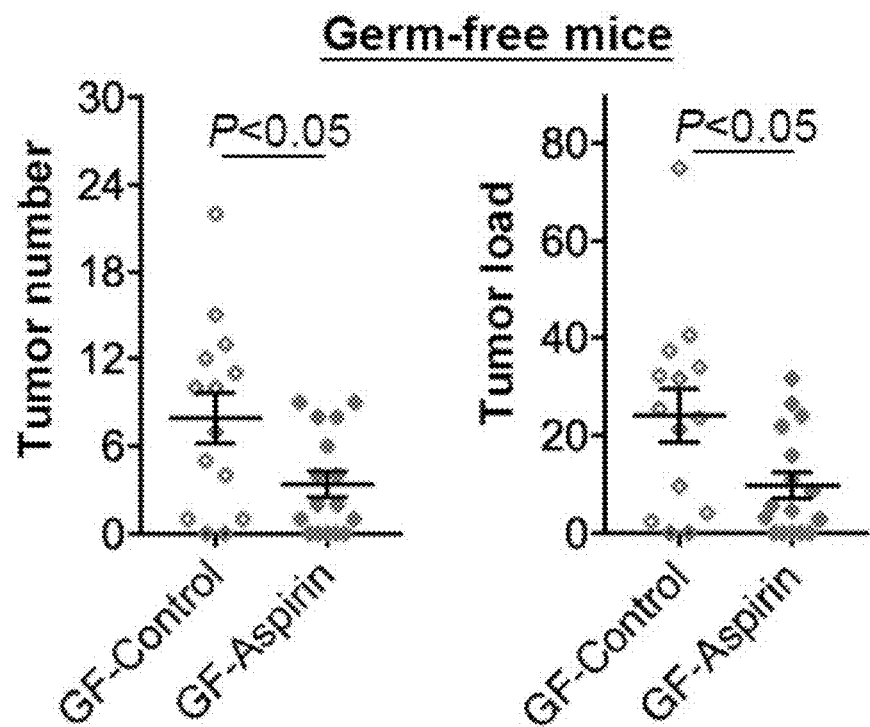
Figure 2D:
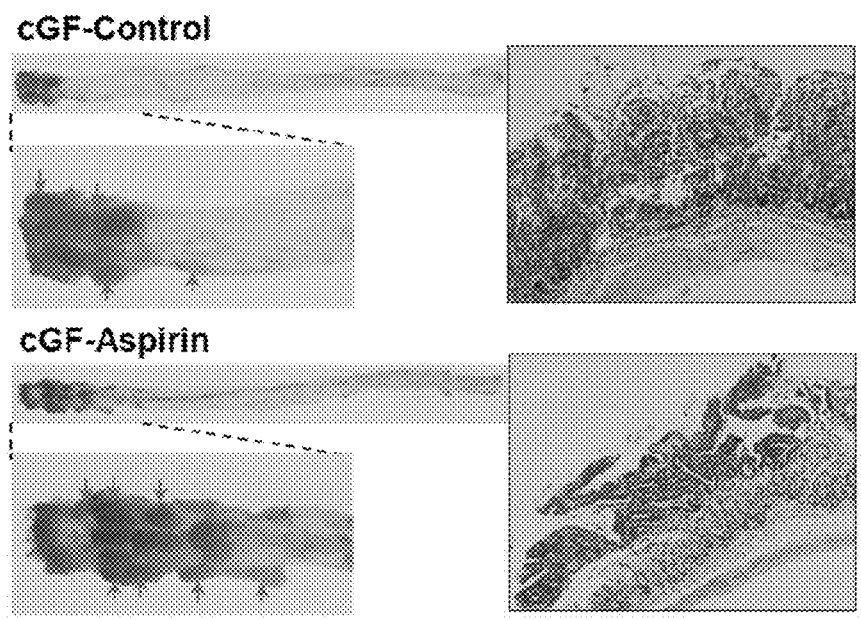
Figure 2E:
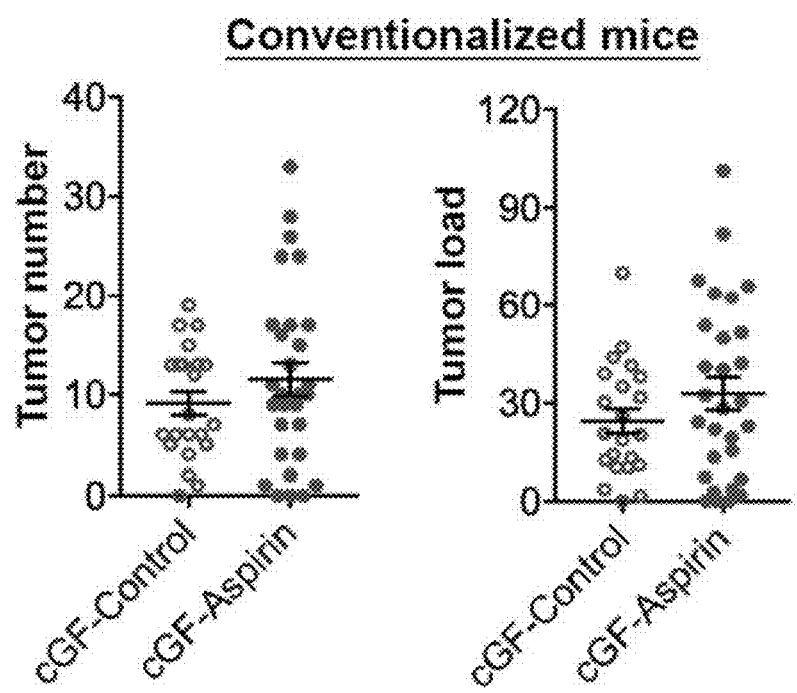

To further validate the impact of gut microbiota on the prevention of CRC by aspirin, colorectal tumorigenesis induced by AOM/DSS in germ-free mice was evaluated (FIG. 2A). As expected, aspirin significantly reduced colorectal tumor number and load in germ-free mice relative to untreated germ-free control mice (FIGS. 2B and C). The suppressive effect of aspirin on tumorigenesis was, however, impaired by conventionalization of the germ-free mice (FIGS. 2D and E). This further confirmed that depletion of microbiota enhanced the chemopreventive efficacy of aspirin on colorectal tumorigenesis.

Gut Microbiota Dampens the Inhibitory Effect of Aspirin on COX-2 and PGE2

Figure 3A:
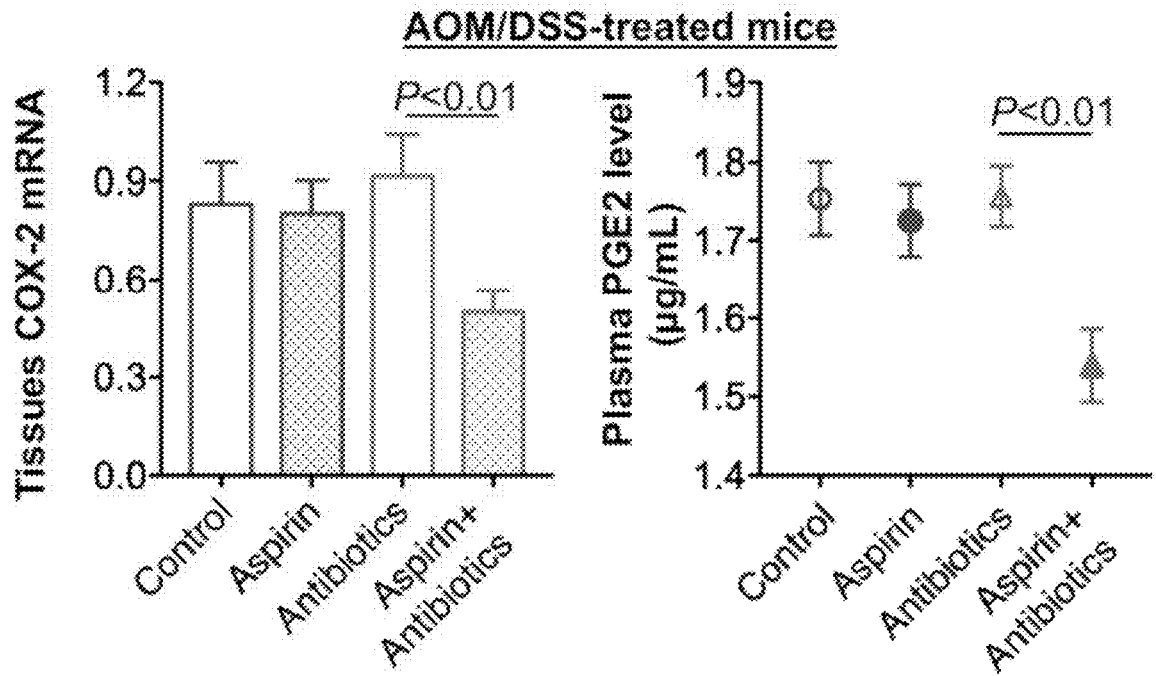
Figure 3B:
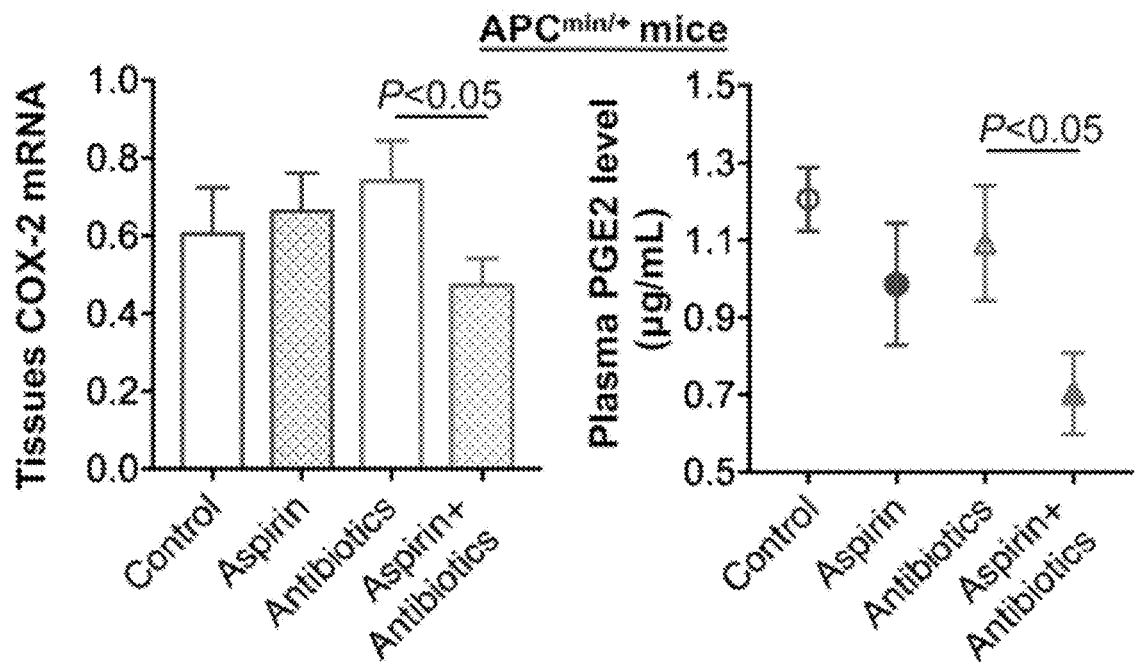
Figure 3C:
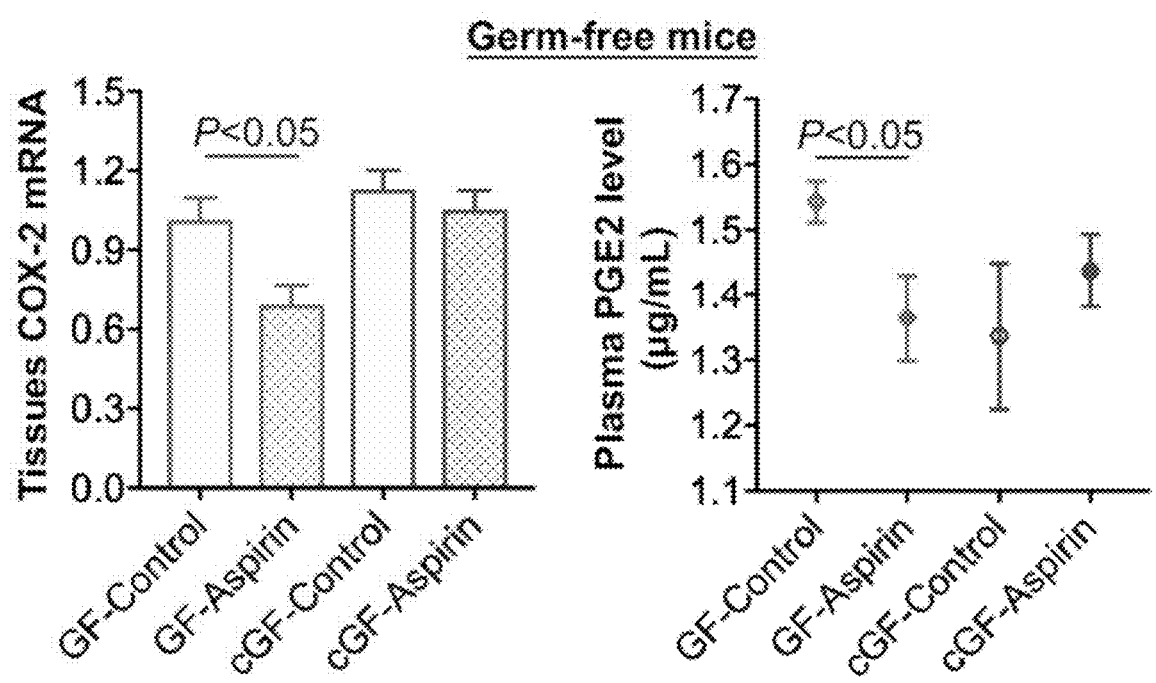

The prevention of CRC by aspirin is associated with its inhibition of COX-2 expression and COX-2-catalyzed PGE2 production[2,3]. The effect of aspirin on colonic tissue COX-2 expression and plasma PGE2 level was therefore determined in microbiota-depleted and germ-free mice. Treatment with aspirin resulted in significantly decreased levels of colonic COX-2 mRNA and plasma PGE2 in both AOM/DSS (FIG. 3A) and $APC^{min/+}$ mice with depleted microbiota (FIG. 3B). Consistently, reductions of COX-2 expression and plasma PGE2 level were observed in AOM/DSS-treated germ-free mice (FIG. 3C). However, there were no differences in the levels of tissue COX-2 expression and plasma PGE2 in conventional mice with intact microbiota and conventionalized germ-free mice compared to control mice (FIG. 3A-C). Thus, the decreased CRC tumorigenesis in microbiota-depleted mice was associated with reduced inhibitory effect of aspirin on COX-2 and PGE2, further indicating that the gut microbiota modulates the therapeutic efficacy of aspirin.

Bioavailability of Aspirin is Elevated in Microbiota-Depleted Mice

Figure 4A:
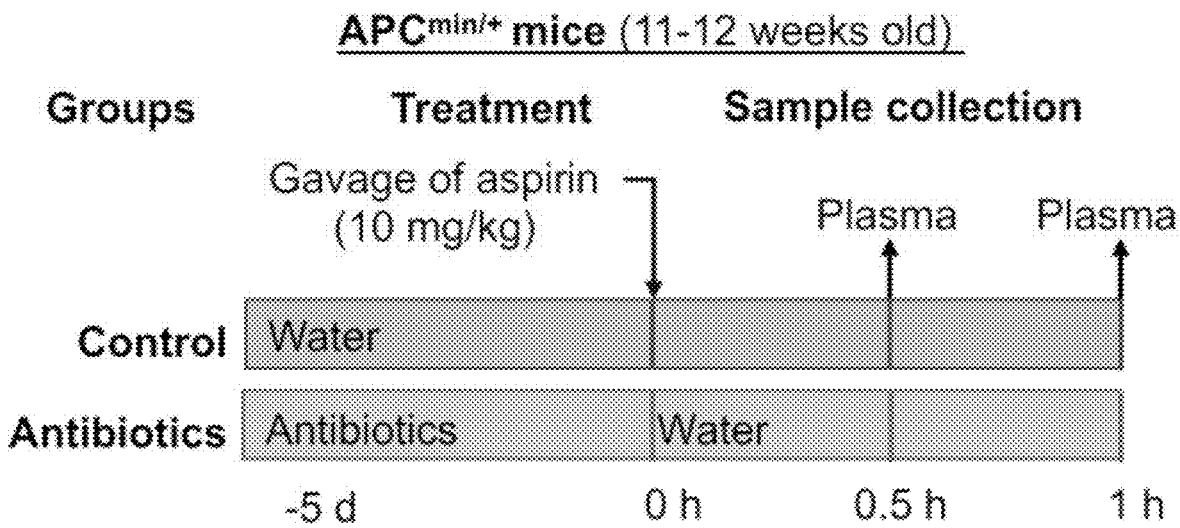
Figure 4B:
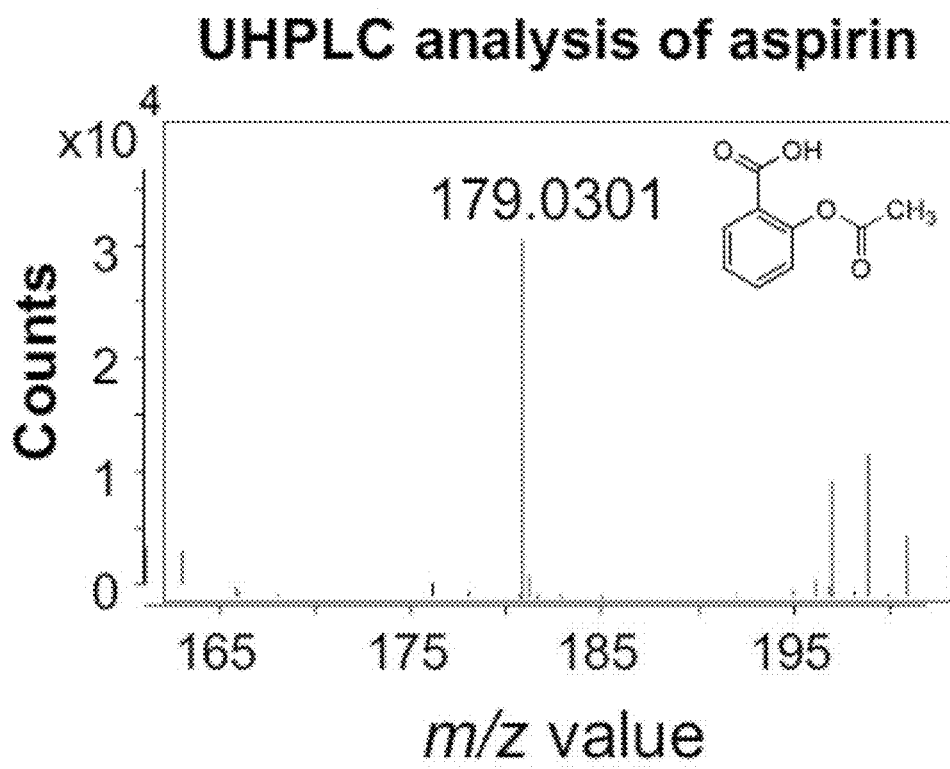
Figure 4C:
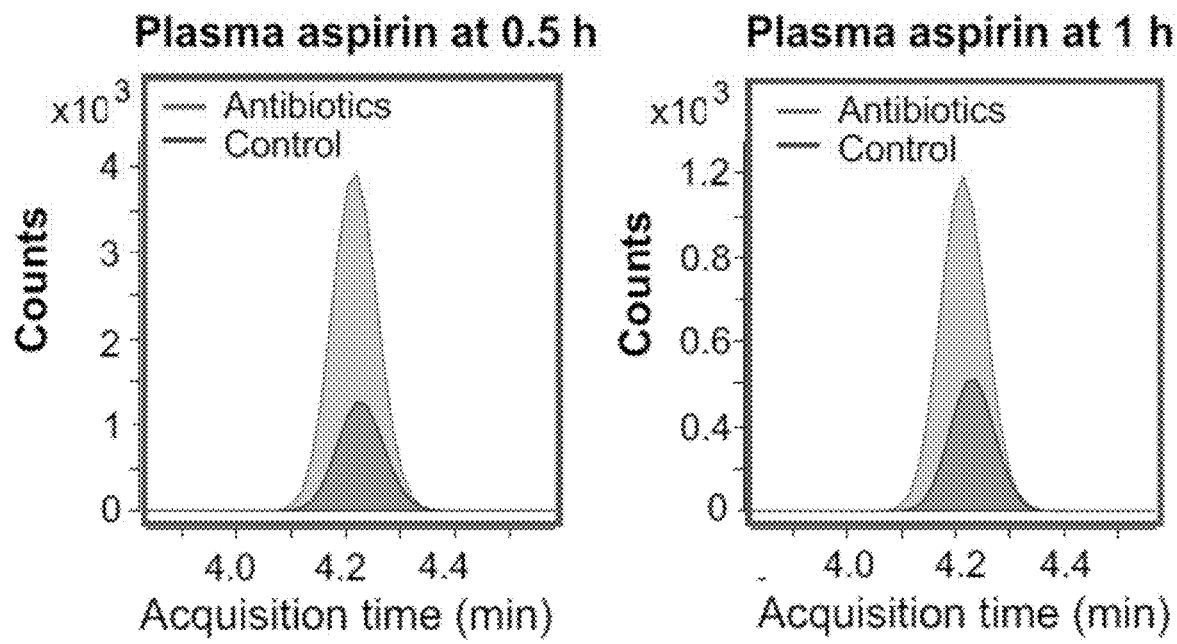
Figure 4D:
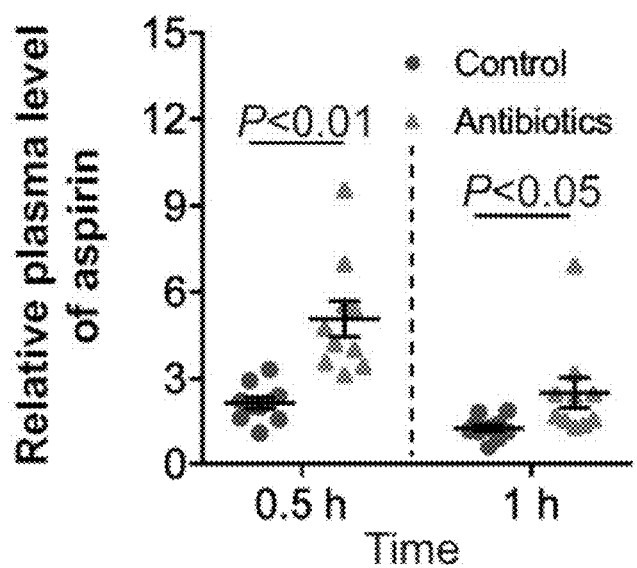

To determine the reason for the enhanced CRC inhibitory effect of aspirin in microbiota-depleted mice, the plasma level of aspirin was evaluated in mice with or without intact microbiota. Antibiotics cocktail was administered to $APC^{min/+}$ mice for five days followed by oral administration of aspirin (10 mg/kg) (FIG. 4A), and subsequent UHPLC-Q-TOF/MS analysis (FIG. 4B). It was discovered that the plasma level of aspirin was significantly increased at both 0.5 h and 1 h post aspirin administration in antibiotics-treated mice relative to mice with intact microbiota (FIGS. 4C and D). To confirm this observation, the level of salicylic acid, the primary metabolite of aspirin, was evaluated in the plasma. The plasma level of salicylic acid increased at 1 h post aspirin administration in microbiota-depleted mice compared to mice with intact microbiota (FIG. 9). These findings indicate that the gut microbiota is associated with the reduction of aspirin bioavailability.

Enhanced Bioavailability Contributes to the Chemopreventive Efficacy of Aspirin

Figure 4E:
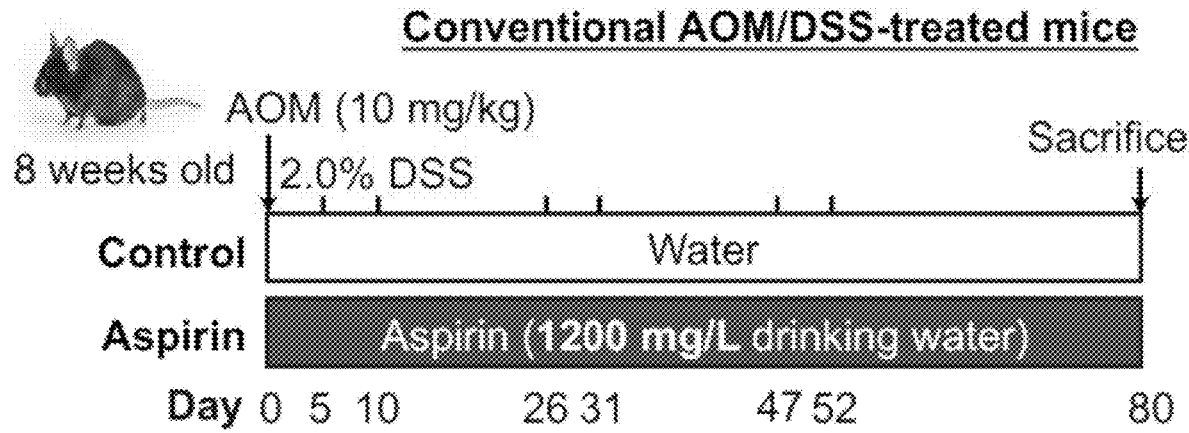
Figure 4F:
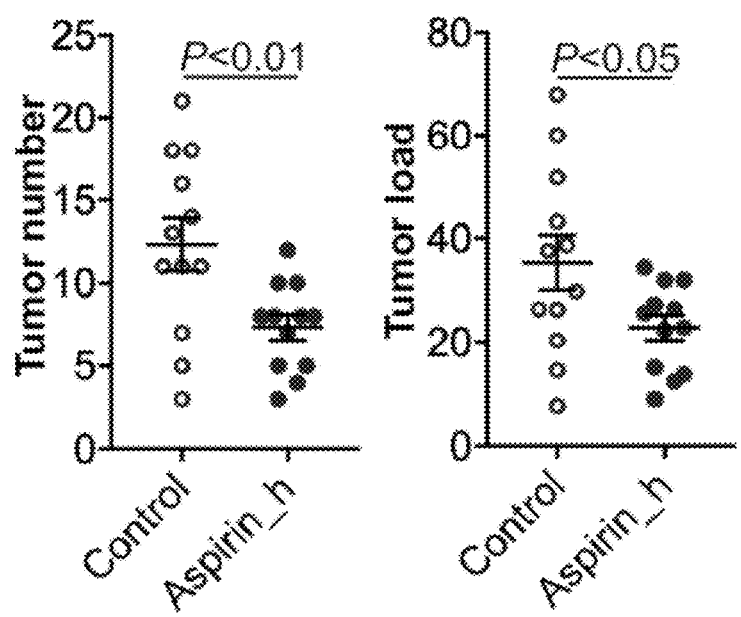

It was further investigated whether the bioavailability of aspirin is associated with its chemopreventive effect on CRC. A higher dose of aspirin (1200 mg/L in drinking water) was administered to AOM/DSS-treated mice (FIG. 4E). In contrast to the observations in microbiota-intact mice that received lower dose of aspirin (400 mg/L in drinking water) (FIG. 1C), it was found significantly reduced colorectal tumor number and load in microbiota-intact mice treated with higher dose of aspirin compared to mice without aspirin treatment (FIG. 4F), suggesting that the bioavailability of aspirin is associated with its protective effect against CRC.

Gut Aerotolerant Microbes are Associated with Aspirin Degradation

Figure 5A:
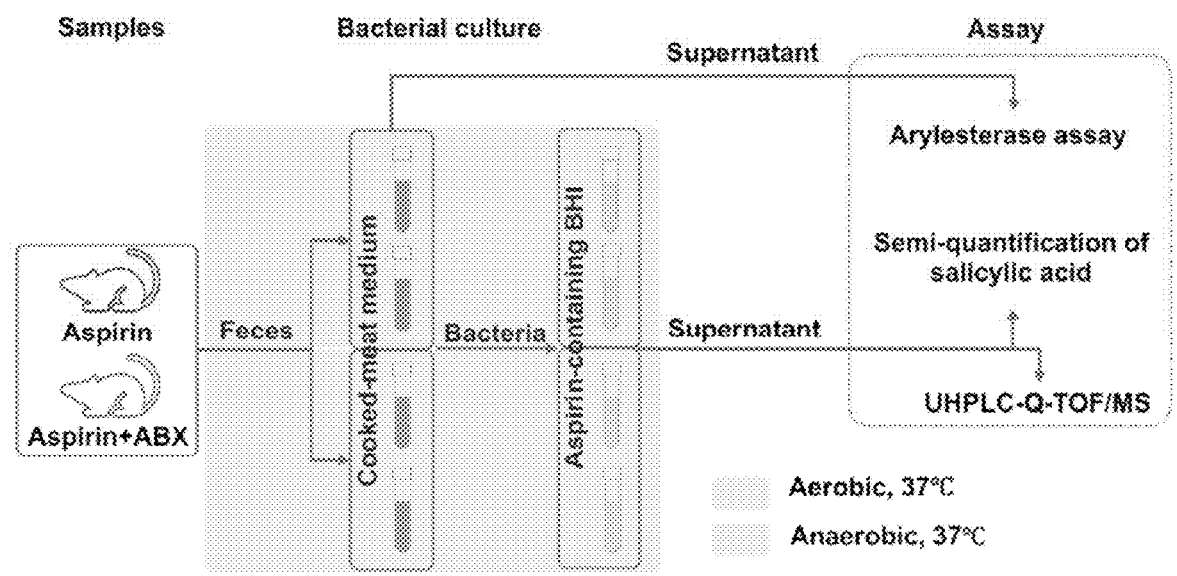
Figure 5B:
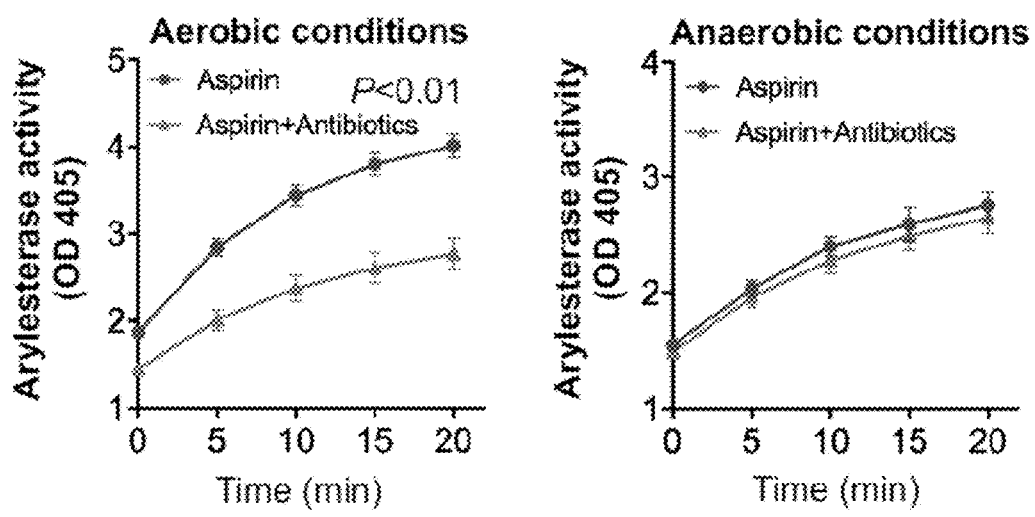
Figure 5C:
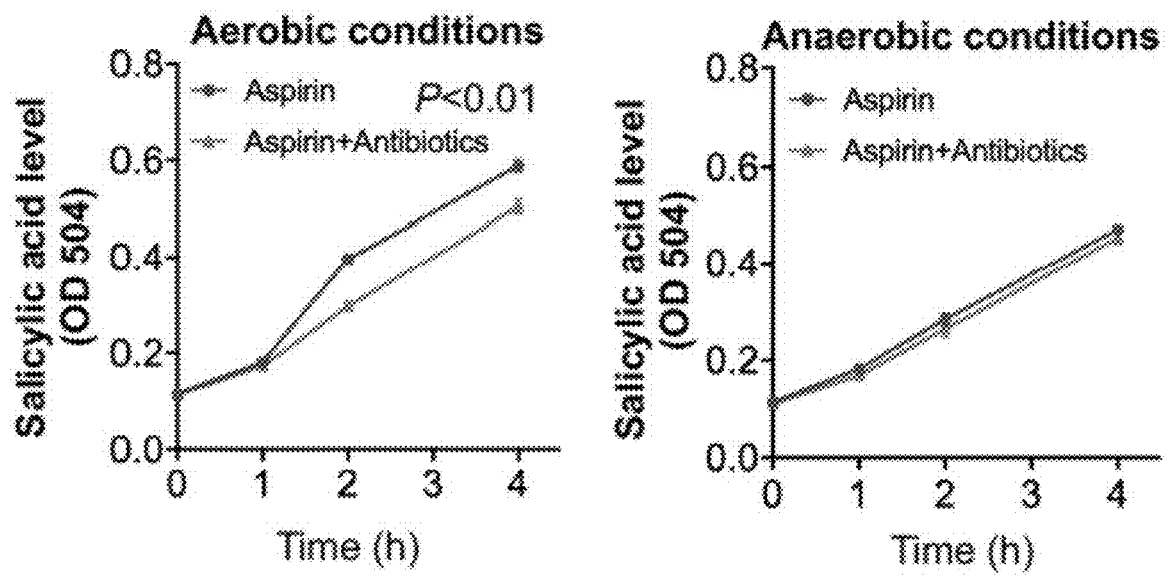
Figure 5D:
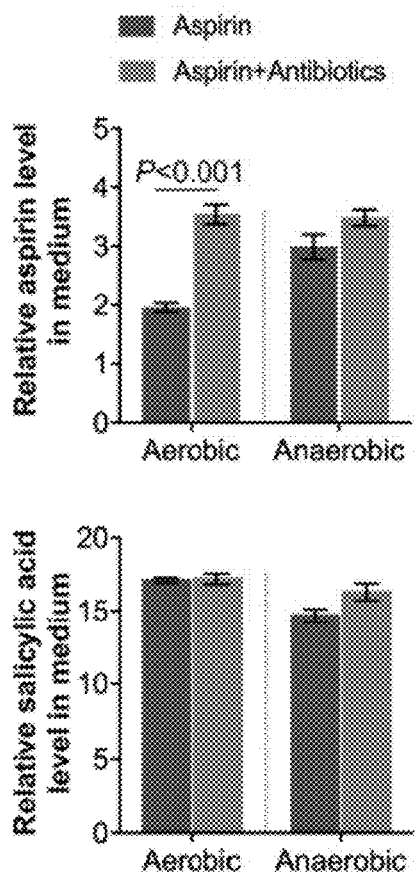

With the observation that the gut microbiota impairs the preventive effect of aspirin on CRC by reducing its bioavailability, gut microbes with aspirin-degradation potential were screened for. Fecal samples from aspirin-treated $APC^{min/+}$ mice were cultured in CM medium and subsequently in aspirin-containing BHI medium under aerobic and anaerobic conditions, followed by examination of the degradation effect on aspirin in the medium (FIG. 5A). It was discovered that arylesterase activity, depicting aspirin degradation, was significantly higher in the medium exposed to fecal samples from antibiotics-naive mice than from antibiotics-treated mice under aerobic culture condition (FIG. 5B). However, the difference was not observed under anaerobic culture condition (FIG. 5B). Additionally, the salicylic acid level in the aspirin-containing medium was significantly lower when co-incubated with fecal samples from antibiotics-treated mice compared to antibiotics-naive mice under aerobic culture condition, but not under anaerobic condition (FIG. 5C). Consistently, UHPLC-Q-TOF/MS analysis showed that the aspirin level in the culture medium was significantly lower after exposure to the fecal samples from antibiotics-naive mice than from antibiotics-treated mice under aerobic culture condition, but not anaerobic culture condition (FIG. 5D). However, the salicylic acid level in the medium was not significantly different between the two groups under both aerobic and anaerobic culture conditions (FIG. 5D). These results collectively indicate that enteric aerotolerant microbes are involved in aspirin degradation.

*Lysinibacillus sphaericus* Degrades Aspirin In Vitro and In Vivo

Figure 6A:
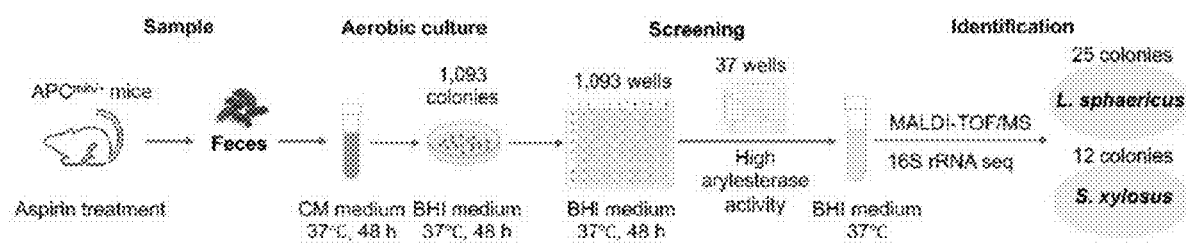
Figure 6B:
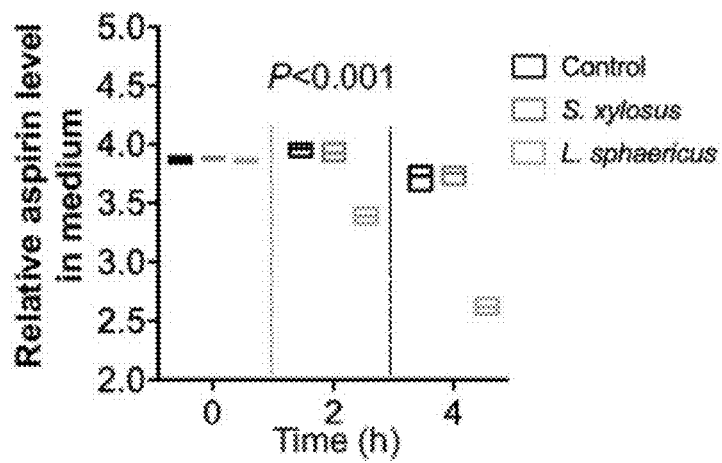

To identify specific gut microbes important in aspirin degradation, the fecal samples from aspirin-treated microbiota-intact $APC^{min/+}$ mice were screened under aerobic culture condition (FIG. 6A). A total of 1,093 bacterial colonies were isolated, of which 37 showed high arylesterase activity relative to blank culture medium. Combination of mass spectrometry and 16S rRNA gene sequencing confirmed that 25 colonies were *Lysinibacillus sphaericus*, while 12 colonies were *Staphylococcus xylosus* (FIG. 6A). Shotgun metagenomic sequencing showed that the abundance of *L. sphaericus*, but not *S. xylosus*, was significantly reduced by antibiotics treatment (FIG. 10A). In vitro incubation of *L. sphaericus* with antibiotics revealed that ampicillin was the key component of the antibiotics cocktail inhibiting the growth of *L. sphaericus* (FIG. 10B). To confirm if *L. sphaericus* and *S. xylosus* could degrade aspirin, each bacterium was aerobically incubated in aspirin-containing medium for 2 hours. Interestingly, *L. sphaericus*, but not *S. xylosus*, was observed to significantly reduced aspirin level in the medium (FIG. 6B). These findings indicate that *L. sphaericus* has the ability to degrade aspirin in vitro.

Figure 6C:
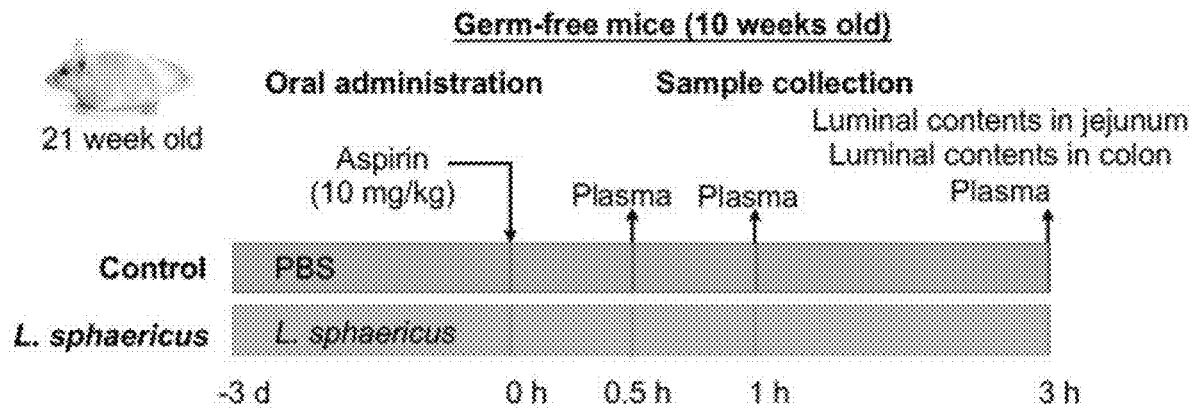
Figure 6D:
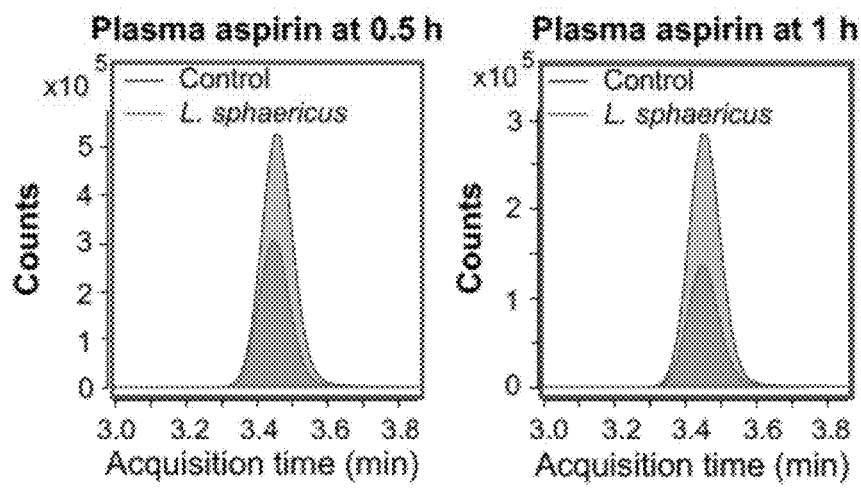
Figure 6E:
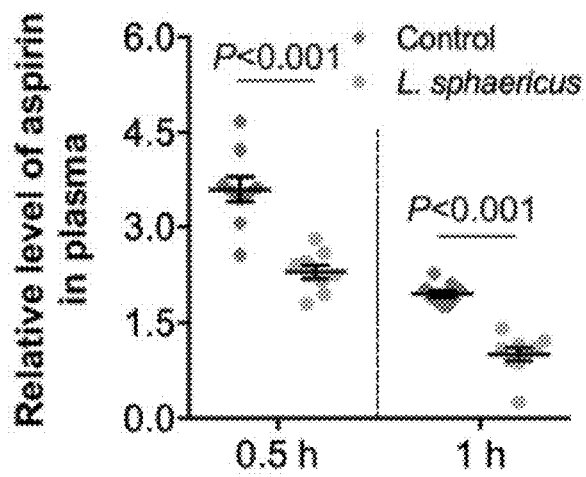

In order to determine whether *L. sphaericus* can degrade aspirin and impacts its bioavailability in vivo, germ-free mice were gavaged with *L. sphaericus* ($1\times10^8$ CFU) once/day for three days, followed by oral administration of aspirin (10 mg/kg) (FIG. 6C). It was found that the plasma level of aspirin was significantly reduced in *L. sphaericus*-monocolonized germ-free mice compared with control germ-free mice at both 0.5 h and 1 h post aspirin administration (FIGS. 6D and E). Moreover, the plasma level of salicylic acid was significantly lowered in *L. sphaericus*-monocolonized mice at 3 h post aspirin administration (FIG. 11A). In accordance with this, the level of salicylic acid in the colon luminal content was also significantly reduced at 3 h post aspirin administration in *L. sphaericus*-monocolonized mice compared to control germ-free mice (FIG. 11B), suggesting that *L. sphaericus* may exert further degradation effect on salicylic acid. Taken together, these findings from in vitro and in vivo experiments indicate that *L. sphaericus* causes aspirin degradation in the gut, thereby reducing aspirin bioavailability.

Figure 6F:
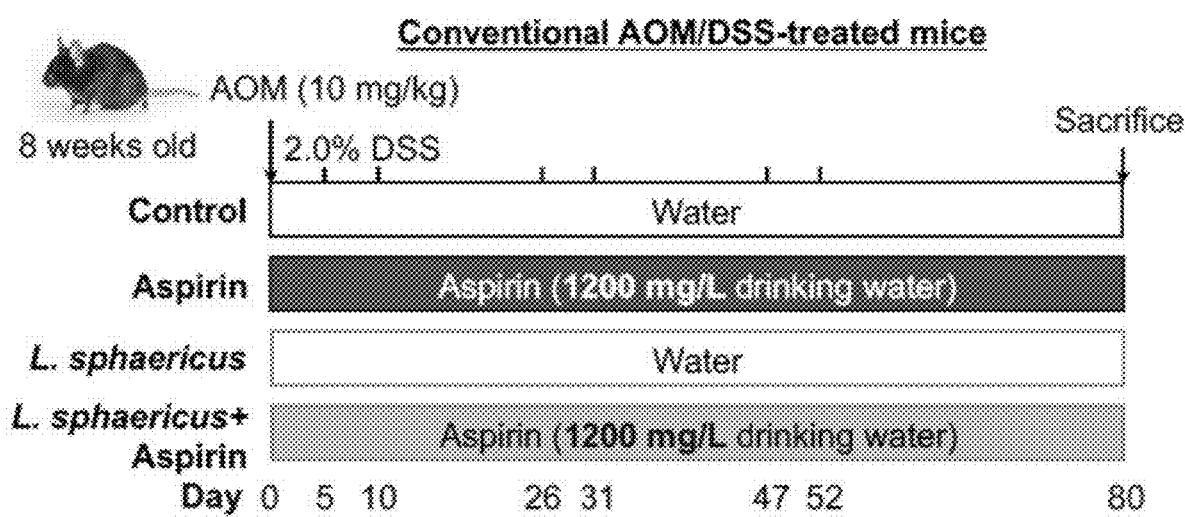
Figure 6G:
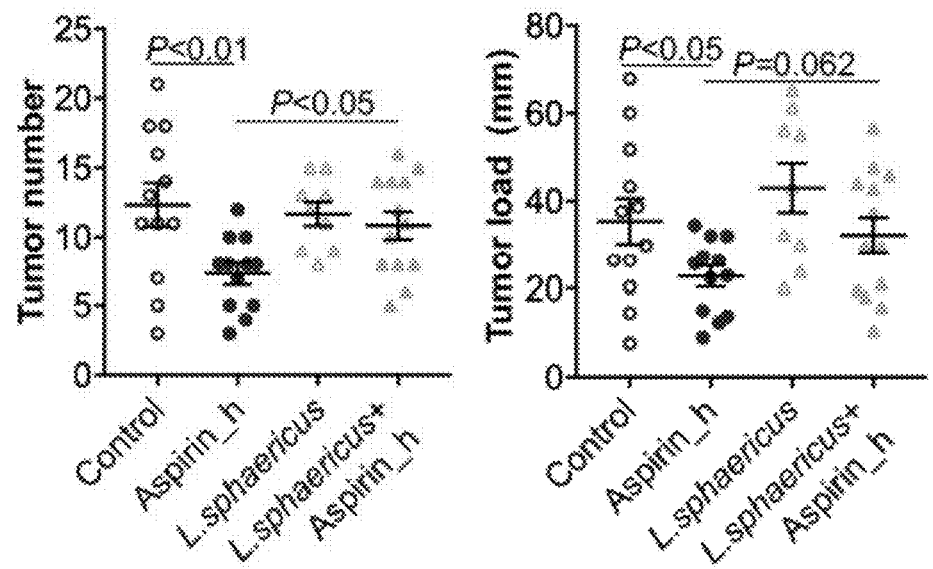
Figure 6H:
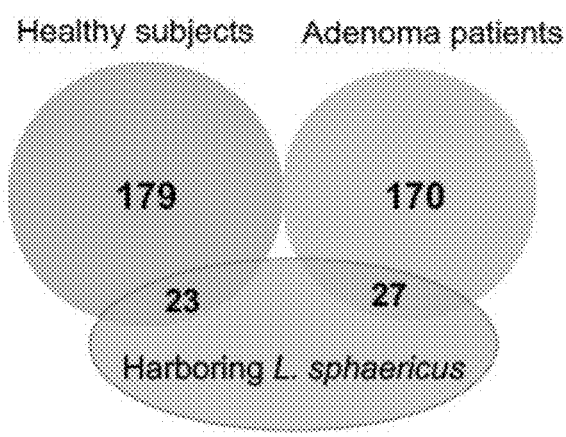

*Lysinibacillus sphaericus* Impairs the Chemopreventive Efficacy of Aspirin on CRC The influence of *L. sphaericus* on CRC chemopreventive efficacy of aspirin in vivo was further evaluated by gavaging conventional AOM/DSS-treated mice receiving high-dose aspirin (1200 mg/L) with *L. sphaericus* ($1\times10^9$ CFU, twice/week) (FIG. 6F). It was observed that *L. sphaericus* impaired the preventive effect of high-dose aspirin on tumor number, albeit marginally on tumor load (FIG. 6G), confirming the role of *L. sphaericus* in dampening the CRC preventive effect of aspirin. The inventors further analyzed their in-house human fecal metagenomic data from healthy subjects and adenoma patients. The analysis revealed that *L. sphaericus* is highly variable among individuals with presence in only 23/202 of healthy patients and 27/197 of adenoma patients (FIG. 6H). This may provide an explanation for the variability of CRC chemopreventive efficacy of aspirin in human.

Aspirin Modulates the Gut Microbiota by Enrichment of Probiotics

Having established the CRC chemoprevention activity of aspirin with increased bioavailability, the present inventors aimed to decipher the potential of the gut microbiota in mediating its protective effect against colorectal tumorigenesis. Shot-gun metagenomics analysis of fecal samples from antibiotics-naive aspirin-treated APC$^{min/+}$ and control mice was performed. Multivariate component analysis showed significant associations between microbial community composition and aspirin treatment (FIG. 7A). With linear discriminant analysis effect size, the enrichment of *Bifidobacterium* and *Lactobacillus* genera in aspirin-treated mice was discovered compared to control (FIG. 7B). Other bacterial genera including *Clostridium* and *Clostridiodes* were depleted in aspirin-treated mice (FIG. 7B). At the species level, probiotics including *Bifidobacterium pseudolongum, B. breve, B. animalis, Lactobacillus reuteri, L. gasseri* and *L. johnsonii* were enriched with aspirin treatment (FIG. 7C). These results indicate that the enrichment of gut protective bacteria by aspirin may represent a mechanism through which aspirin contributes to CRC prevention.

Discussion

It is becoming increasingly evident that the gut microbiota is actively involved in CRC development. Here, the present inventors utilized conventional and germ-free mouse models to bridge the knowledge gap between the gut microbiota and the efficacy of CRC chemoprevention by aspirin. Intestinal tumorigenesis in mice was induced by AOM/DSS and mutation of APC gene. CRC chemoprevention by aspirin was demonstrated in both models with gut microbiota depletion, but not with intact gut microbiota. Emerging evidence shows that antibiotic treatment modulates host metabolism and intestinal gene expression[30], indicating a potential role of antibiotics in influencing tumorigenesis. To avoid obscuring the chemopreventive effect of aspirin by antibiotics, germ-free mouse model was further employed. Consistently, aspirin inhibited colorectal tumorigenesis in germ-free mice. Yet, this inhibitory effect was impaired by conventionalization of the germ-free mice. These findings collectively highlight the role of gut microbiota in modulating the chemopreventive efficacy of aspirin on CRC.

The aspirin-mediated CRC chemoprevention in antibiotics-treated conventional mice and germ-free mice was further demonstrated to be associated with enhanced suppression of colonic COX-2 expression and plasma PEG2 level. This is consistent with the reports that inhibition of COX-2 and PGE2 contributes to CRC chemopreventive efficacy of aspirin.[2,3] Notably, the suppressive effects of COX-2 and PGE2 by aspirin are dose-dependent[31,32]. Given that aspirin is primarily absorbed in the upper gastrointestinal (GI) tract[33,34], it was examined if the suppressive effect of colorectal tumorigenesis depends on the level of aspirin in circulation. The plasma level of aspirin was significantly elevated post aspirin administration in mice with depleted microbiota compared with microbiota-intact mice. Moreover, increasing aspirin bioavailability by administration of a higher dose of aspirin restored the chemopreventive effectiveness of aspirin in AOM/DSS-treated conventional mice. This confirms the importance of aspirin bioavailability on CRC chemoprevention. This finding is supported by reports that certain cumulative dose of aspirin is needed to attain the effectiveness of aspirin on CRC chemoprevention in human[9,35]. Taken together, this study demonstrates that the gut microbiota impairs the chemopreventive efficacy of aspirin on CRC by reducing its bioavailability.

To unravel the effect of bacteria on aspirin, aspirin was co-incubated with fecal samples under aerobic and anaerobic conditions. Fecal microbiota from antibiotics-naive mice significantly decreased the level of aspirin in culture medium under aerobic, but not anaerobic, conditions. This indicates that gut aerobes or facultative anaerobes are important in aspirin degradation. *L. sphaericus*, an aerobic and spore-forming bacterium[36,37], was identified by high-throughput screening to be the predominant microbe in aspirin degradation. These in-vivo studies demonstrate that the gut colonization by this bacterium reduces plasma aspirin level and compromises the CRC chemopreventive effect of aspirin. Analysis of available human fecal metagenomics sequencing data[10] showed that 11.4% of healthy individuals harbor *L. sphaericus* in the gut. This may provide an explanation for the reported variableness of CRC chemoprevention by aspirin in human[8,9]. Further studies are needed to evaluate the impact of *L. sphaericus* and its impact on the outcomes of aspirin-mediated CRC chemoprevention. This will allow a better understanding of the role of this microbe and might inform personalized medicine in human CRC chemoprevention by aspirin.

As a potential mediator of aspirin-induced CRC chemoprevention, the enrichment of *Bifidobacterium* and *Lactobacillus* was observed in aspirin-treated mice. The protective effects of probiotics on CRC have been reported[38,39]. Aspirin treatment resulted in the accumulation of well-characterized probiotic species including *B. pseudolongum, B. breve, B. animalis, L. reuteri, L. gasseri* and *L. johnsonii* in this study. An unbalanced gut microbial structure may trigger or promote colorectal tumorigenesis[11,40]. On the other hand, daily consumption of probiotics has been shown to restore microbiota homeostasis and inhibit the colonization of the gut by carcinogenic pathogens[41,42]. It is therefore plausible that the enhanced enrichment of probiotic species by aspirin might contribute to its CRC protective effect.

In conclusion, this study for the first time demonstrated that the gut microbiota, such as *L. sphaericus*, modulates the chemopreventive efficacy of aspirin on CRC by influencing its bioavailability in mice. Aspirin treatment leads to the enrichment of gut probiotics, which may additionally contribute to its CRC protective effect.

All patents, patent applications, and other publications, including GenBank Accession Numbers, cited in this application are incorporated by reference in the entirety for all purposes.

REFERENCES

1. Arnold M, Sierra M S, Laversanne M, et al. Global patterns and trends in colorectal cancer incidence and mortality. Gut 2017; 66:683-691.
2. Thun M J, Jacobs E J, Patrono C. The role of aspirin in cancer prevention. Nat Rev Clin Oncol 2012; 9:259-267.
3. Drew D A, Cao Y, Chan A T. Aspirin and colorectal cancer: the promise of precision chemoprevention. Nat Rev Cancer 2016; 16:173-186.
4. Baron J A, Cole B F, Sandler R S, et al. A randomized trial of aspirin to prevent colorectal adenomas. N Engl J Med 2003; 348:891-899.
5. Burn J, Gerdes A-M, Macrae F, et al. Long-term effect of aspirin on cancer risk in carriers of hereditary colorectal cancer: an analysis from the CAPP2 randomised controlled trial. Lancet 2011; 378:2081-2087.
6. Hull M A, Sprange K, Hepburn T, et al. Eicosapentaenoic acid and aspirin, alone and in combination, for the prevention of colorectal adenomas (seAFOod Polyp Prevention trial): a multicentre, randomised, double-blind, placebo-controlled, 2×2 factorial trial. Lancet 2018; 392: 2583-2594.
7. Chubak J, Kamineni A, Buist D S, et al. Aspirin use for the prevention of colorectal cancer: an updated systematic evidence review for the U.S. Preventive Services Task Force. Rockville (Md.): Agency for Healthcare Research and Quality (US); 2015; 15-05228-EF-1.
8. Rothwell P M, Cook N R, Gaziano J M, et al. Effects of aspirin on risks of vascular events and cancer according to bodyweight and dose: analysis of individual patient data from randomised trials. Lancet 2018; 392:387-399.
9. Chan A T, Giovannucci E L, Meyerhardt J A, et al. Aspirin dose and duration of use and risk of colorectal cancer in men. Gastroenterology 2008; 134:21-28.
10. Yu J, Feng Q, Wong S H, et al. Metagenomic analysis of faecal microbiome as a tool towards targeted non-invasive biomarkers for colorectal cancer. Gut 2017; 66:70-78.
11. Nakatsu G, Li X, Zhou H, Sheng J, Wong S, Wu W, et al. Gut mucosal microbiome across stages of colorectal carcinogenesis. Nat Commun 2015; 6:8727.
12. Tsoi H, Chu E S H, Zhang X, et al. *Peptostreptococcus anaerobius* induces intracellular cholesterol biosynthesis in colon cells to induce proliferation and causes dysplasia in mice. Gastroenterology 2017; 152:1419-1433.e5.
13. Wong S H, Zhao L, Zhang X, et al. Gavage of fecal samples from patients with colorectal cancer promotes intestinal carcinogenesis in germ-free and conventional mice. Gastroenterology 2017; 153:1621-1633.e6.
14. David L A, Maurice C F, Carmody R N, et al. Diet rapidly and reproducibly alters the human gut microbiome. Nature 2014; 505:559-563.
15. Thaiss C A, Levy M, Korem T, et al. Microbiota diurnal rhythmicity programs host transcriptome oscillations. Cell 2016; 167:1495-1510.e12.
16. Wang Y, Kuang Z, Yu X, et al. The intestinal microbiota regulates body composition through NFIL3 and the circadian clock. Science 2017; 357:912-916.
17. Maier L, Pruteanu M, Kuhn M, et al. Extensive impact of non-antibiotic drugs on human gut bacteria. Nature 2018; 555:623-628.
18. Wu H, Esteve E, Tremaroli V, et al. Metformin alters the gut microbiome of individuals with treatment-naive type 2 diabetes, contributing to the therapeutic effects of the drug. Nat Med 2017; 23:850-858.
19. Cheng X, Huang F, Zhang K, et al. Effects of nonesteroidal anti-inflammatory and antibiotic drugs on the oral immune system and oral microbial composition in rats. Biochem Biophys Res Commun 2018; 507:420-425.
20. Rogers M a. M, Aronoff D M. The influence of nonsteroidal anti-inflammatory drugs on the gut microbiome. Clin Microbiol Infect 2016; 22:178.e1-178.e9.
21. Koppel N, Rekdal V M, Balskus E P. Chemical transformation of xenobiotics by the human gut microbiota. Science 2017; 356:eaag2770.
22. Sousa T, Yadav V, Zann V, et al. On the colonic bacterial metabolism of azo-bonded prodrugs of 5-aminosalicylic acid. J Pharm Sci 2014; 103:3171-3175.
23. Haiser H J, Gootenberg D B, Chatman K, et al. Predicting and manipulating cardiac drug inactivation by the human gut bacterium *Eggerthella lenta*. Science 2013; 341:295-298.
24. Kim I S, Yoo D H, Jung I H, et al. Reduced metabolic activity of gut microbiota by antibiotics can potentiate the antithrombotic effect of aspirin. Biochem Pharmacol 2016; 122:72-79.
25. Reddy B S, Rao C V, Rivenson A, et al. Inhibitory effect of aspirin on azoxymethane-induced colon carcinogenesis in F344 rats. Carcinogenesis 1993; 14:1493-1497.
26. Trinder P. Rapid determination of salicylate in biological fluids. Biochem J 1954; 57:301-303.
27. Nakatsu G, Zhou H, Wu W K K, et al. Alterations in enteric virome are associated with colorectal cancer and survival outcomes. Gastroenterology 2018; 155:529-541.e5.
28. Coker O O, Nakatsu G, Dai R Z, et al. Enteric fungal microbiota dysbiosis and ecological alterations in colorectal cancer. Gut 2019; 68:654-662.
29. Edalatian M R, Najafi M B H, Mortazavi S A, et al. Microbial diversity of the traditional Iranian cheeses Lighvan and Koozeh, as revealed by polyphasic culturing and culture-independent approaches. Dairy Sci Technol 2012; 92:75-90.
30. Zarrinpar A, Chaix A, Xu Z Z, et al. Antibiotic-induced microbiome depletion alters metabolic homeostasis by affecting gut signaling and colonic metabolism. Nat Commun 2018; 9:2872.
31. Xu X M, Sansores-Garcia L, Chen X M, et al. Suppression of inducible cyclooxygenase 2 gene transcription by aspirin and sodium salicylate. PNAS 1999; 96:5292-5297.
32. Fiebich B L, Lieb K, Hüll M, et al. Effects of caffeine and paracetamol alone or in combination with acetylsalicylic acid on prostaglandin E2 synthesis in rat microglial cells. Neuropharmacology 2000; 39:2205-2213.
33. Salter R H. Aspirin and gastrointestinal bleeding. Am J Dig Dis 1968; 13:38-58.
34. Hollander D, Dadufalza V D, Fairchild P A. Intestinal absorption of aspirin. Influence of pH, taurocholate, ascorbate, and ethanol. J Lab Clin Med 1981; 98:591-598.
35. Rodriguez LAG, Huerta-Alvarez C. Reduced risk of colorectal cancer among long-Term users of aspirin and nonaspirin nonsteroidal antiinflammatory drugs. Epidemiology 2001; 12:88-93.
36. Shi T, Ge Y, Zhao N, et al. Polyphosphate kinase of *Lysinibacillus sphaericus* and its effects on accumulation of polyphosphate and bacterial growth. Microbiol Res 2015; 172:41-47.
37. Ahmed I, Yokota A, Yamazoe A, et al. Proposal of *Lysinibacillus boronitolerans* gen. nov. sp. nov., and transfer of *Bacillus fusiformis* to *Lysinibacillus fusiformis* comb. nov. and *Bacillus sphaericus* to *Lysinibacillus sphaericus* comb. nov. Int J Syst Evol Microbiol 2007; 57:1117-1125.
38. Chen X, Fruehauf J, Goldsmith J D, et al. *Saccharomyces boulardii* inhibits EGF receptor signaling and intestinal tumor growth in Apc(min) mice. Gastroenterology 2009; 137:914-923.
39. Konishi H, Fujiya M, Tanaka H, et al. Probiotic-derived ferrichrome inhibits colon cancer progression via JNK-mediated apoptosis. Nat Commun 2016; 7:12365.
40. Dai Z, Coker O O, Nakatsu G, Wu K, et al. Multi-cohort analysis of colorectal cancer metagenome identified altered bacteria across populations and universal bacterial markers. Microbiome 2018; 6:70.
41. Ishikawa H, Akedo I, Otani T, et al. Randomized trial of dietary fiber and *Lactobacillus casei* administration for prevention of colorectal tumors. Int J Cancer 2005; 116:762-767.
42. Rafter J, Bennett M, Caderni G, et al. Dietary synbiotics reduce cancer risk factors in polypectomized and colon cancer patients. Am J Clin Nutr 2007; 85:488-496.

What is claimed is:

1. A method for reducing colorectal cancer (CRC) risk in an individual, comprising the steps of:
   (1) performing metagenomic sequencing to detect the presence or absence of *Lysinibacillus sphaericus* in a stool sample taken from the individual; and (2a) determining *Lysinibacillus sphaericus* is not detected in the stool sample, and administering to the individual an effective amount of aspirin; or (2b) determining *Lysinibacillus sphaericus* is detected in the stool sample, and administering to the individual an effective amount of aspirin just after or at the same time of providing an antibiotic treatment that suppresses or eliminates *Lysinibacillus sphaericus* in the individual, wherein the antibiotic treatment does not include treatment with an antisense oligonucleotide or small inhibitory RNA.

2. The method of claim 1, wherein the individual has a family history of CRC or has been diagnosed with colon polyps or cysts.

3. The method of claim 1, wherein *Lysinibacillus sphaericus* level is measured by metagenomic sequencing.

4. The method of claim 1, further comprising a step of determining the level of one or more of *Bifidobacterium pseudolongum, B. breve, B. animalis, Lactobacillus reuteri, L. gasseri*, and *L. johnsonii* in the stool sample.

5. The method of claim 1, wherein *Lysinibacillus sphaericus* is detected in the stool sample, and wherein the individual is administered an effective amount of aspirin just after or at the same time of receiving an antibiotic treatment that suppresses or eliminates *Lysinibacillus sphaericus* in the individual, the method further comprising, after step (2b), a step of detecting *Lysinibacillus sphaericus* in a second stool sample taken from the individual.

6. The method of claim 5, wherein the antibiotic treatment comprises administration of ampicillin.

7. The method of claim 6, wherein the antibiotic treatment comprises administration of ampicillin, neomycin, metronidazole, and vancomycin.

8. A method for reducing CRC risk by aspirin administration among individuals, comprising the steps of:

(a) measuring *Lysinibacillus sphaericus* level in a first stool sample taken from a first individual and in a second stool sample taken from a second individual by metagenomic sequencing;

(b) detecting the *Lysinibacillus sphaericus* level in the first sample as being higher than the *Lysinibacillus sphaericus* level in the second sample; and (c) providing to the first individual an antibiotic treatment that suppresses or eliminates *Lysinibacillus sphaericus* just prior to or at same time of administering to the first individual an effective amount of aspirin, wherein the antibiotic treatment does not include treatment with an antisense oligonucleotide or small inhibitory RNA.

9. The method of claim 8, further comprising, when *Lysinibacillus sphaericus* is not detected in the second sample, administering to the second individual an effective amount of aspirin; or, when *Lysinibacillus sphaericus* is detected in the second sample, providing to the second individual an antibiotic treatment that suppresses or eliminates *Lysinibacillus sphaericus* just prior to or at same time of administering to the second individual an effective amount of aspirin, wherein the antibiotic treatment provided to the second individual does not include treatment with an antisense oligonucleotide or small inhibitory RNA.

10. The method of claim 8, wherein the individuals have a family history of CRC or have been diagnosed with colon polyps or cysts.

11. The method of claim 8, further comprising a step of determining the level of one or more of *Bifidobacterium pseudolongum, B. breve, B. animalis, Lactobacillus reuteri, L. gasseri*, and *L. johnsonii* in the stool samples.

12. The method of claim 8, wherein the antibiotic treatment comprises administration of ampicillin.

13. The method of claim 12, wherein the antibiotic treatment comprises administration of ampicillin, neomycin, metronidazole, and vancomycin.

14. The method of claim 9, wherein the antibiotic treatment provided to the second individual comprises administration of ampicillin.

15. The method of claim 14, wherein the antibiotic treatment comprises administration of ampicillin, neomycin, metronidazole, and vancomycin.

* * * * *